US012662483B2

(12) United States Patent
Coates et al.

(10) Patent No.: US 12,662,483 B2
(45) Date of Patent: Jun. 23, 2026

(54) COCRYSTALLINE FORMS OF FGFR3 INHIBITORS

(71) Applicant: Eli Lilly and Company, Indianapolis, IN (US)

(72) Inventors: David Andrew Coates, New Palestine, IN (US); Lori Raquel Hilden, Indianapolis, IN (US); Gislaine Kuminek, Indianapolis, IN (US); Jeffrey A. Peterson, Carmel, IN (US)

(73) Assignee: Eli Lilly and Company, Indianapolis, IN (US)

(*) Notice: Subject to any disclaimer, the term of this patent is extended or adjusted under 35 U.S.C. 154(b) by 477 days.

(21) Appl. No.: 18/462,286

(22) Filed: Sep. 6, 2023

(65) Prior Publication Data

US 2024/0116932 A1 Apr. 11, 2024

Related U.S. Application Data

(60) Provisional application No. 63/404,232, filed on Sep. 7, 2022.

(51) Int. Cl.
*C07D 471/04* (2006.01)
*C07C 65/05* (2006.01)

(52) U.S. Cl.
CPC ............ *C07D 471/04* (2013.01); *C07C 65/05* (2013.01); *C07B 2200/13* (2013.01)

(58) Field of Classification Search
None
See application file for complete search history.

(56) References Cited

U.S. PATENT DOCUMENTS

| | | | | |
|---|---|---|---|---|
| 11,878,976 | B2 * | 1/2024 | Abraham | C07D 471/04 |
| 12,209,086 | B2 * | 1/2025 | Abraham | C07D 471/04 |
| 2025/0122196 | A1 * | 4/2025 | Abraham | C07D 471/04 |

FOREIGN PATENT DOCUMENTS

| | | | |
|---|---|---|---|
| WO | 2020/131627 | A1 | 6/2020 |
| WO | 2022/187443 | A1 | 9/2022 |

OTHER PUBLICATIONS

International Search Report for PCT/US2023/073508 dated Nov. 21, 2023.
Written Opinion of the International Searching Authority for PCT/US2023/073508 dated Nov. 21, 2023.

* cited by examiner

*Primary Examiner* — Jeffrey S Lundgren
*Assistant Examiner* — Sara Elizabeth Townsley
(74) *Attorney, Agent, or Firm* — Bradley W. Crawford

(57) ABSTRACT

Provided herein are cocrystalline forms of FGFR3 inhibitors and gallic acid or nicotinamide coformers useful in the treatment and prevention of diseases which can be treated with a FGFR3 inhibitor, including FGFR3-associated diseases and disorders, characterizations and methods of making these cocrystalline forms.

63 Claims, No Drawings

COCRYSTALLINE FORMS OF FGFR3 INHIBITORS

This disclosure is directed to the field of cancer treatment.

BACKGROUND

Fibroblast growth factor (FGF) is an important mediator of many physiological processes, such as morphogenesis during development, fibrosis, and angiogenesis. The fibroblast growth factor receptor (FGFR) family consists of five members, four of which (FGFR 1-4) are glycoproteins composed of extracellular immunoglobulin (Ig)-like domains, a hydrophobic transmembrane region and a cytoplasmic part containing a tyrosine kinase domain. FGF binding leads to FGFR dimerization, followed by receptor autophosphorylation and activation of downstream signaling pathways. Receptor activation is sufficient for the recruitment and activation of specific downstream signaling partners that participate in the regulation of diverse processes such as cell growth, cell metabolism and cell survival. Thus, the FGF/FGFR signaling pathway has pleiotropic effects on many biological processes critical to tumor cell proliferation, migration, invasion, and angiogenesis.

It would be useful to develop new forms of FGFR3 inhibitors to treat cancer. It would also be useful to develop improved solid state forms and forms with improved chemical stability. It would be useful to develop forms of FGFR3 inhibitors that improve solubility over current forms of FGFR3 inhibitors, such as freebase versions of a FGFR3 inhibitor. It would be useful to develop forms of FGFR3 inhibitors that have improved chemical stability over current forms of FGFR3 inhibitors, such as SDD forms of a FGFR3 inhibitor. It would be useful to develop forms of FGFR3 inhibitors that improve absorption of FGFR3 inhibitors. It would be useful to develop forms of FGFR3 inhibitors that enable oral administration of FGFR3 inhibitors. It would be useful to develop forms which result in fewer operational process steps, simplification of supply chain, and use of fewer unit operations over current forms of FGFR3 inhibitors, such as SDD forms of a FGFR3 inhibitor. It would be useful to develop forms which use less solvent or require less environmental impact over current forms of FGFR3 inhibitors, such as SDD forms of a FGFR3 inhibitor.

SUMMARY

WO/2022/187443 (International patent application number PCT/US2022/018644) and US2023/0095122 A1 (U.S. patent application Ser. No. 17/685,753) disclose compounds or salts thereof that can be used as FGFR3 inhibitors. An example of an FGFR3 inhibitor disclosed therein is 4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, which has the following structure:

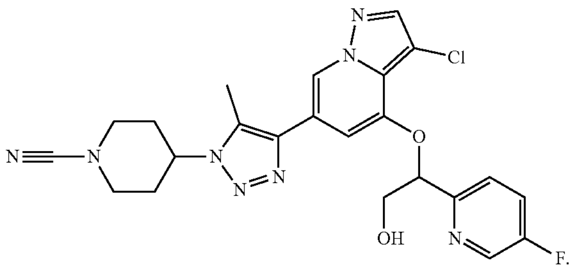 [SMILES: Cc1c(-c2cc(OC(CO)c3ccc(F)cn3)c3c(Cl)cnn3c2)nnn1C1CCN(C#N)CC1]

This compound was disclosed as individual isomers in Examples 45 and 46 of both WO/2022/187443 (International patent application number PCT/US2022/018644) and US2023/0095122 A1 (U.S. patent application Ser. No. 17/685,753). As disclosed therein, this compound exists as isomers. Further as discussed in Examples 45 and 46 of these references, the isomers may be separated using prep-chiral-HPLC. Example 45 is the first isomer to elute, while Example 46 is the second isomer to elute, when separated using an HPLC column: ART Cellulose-SB, 2*25 cm, 5 μm, when eluting with 20% 5:1 Hex:DCM (0.5% 2M $NH_3$ in MeOH) in EtOH.

Example 45, 4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 1, (hereinafter "Isomer 1"), is the R-enantiomer. Isomer 1 has the following structure:

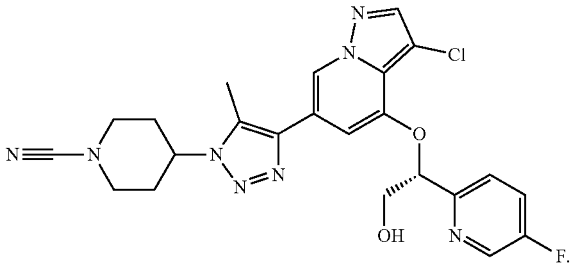 [SMILES: Cc1c(-c2cc(O[C@@H](CO)c3ccc(F)cn3)c3c(Cl)cnn3c2)nnn1C1CCN(C#N)CC1]

Example 46, 4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2, (hereinafter "Isomer 2"), is the S-enantiomer. Isomer 2 has the following structure:

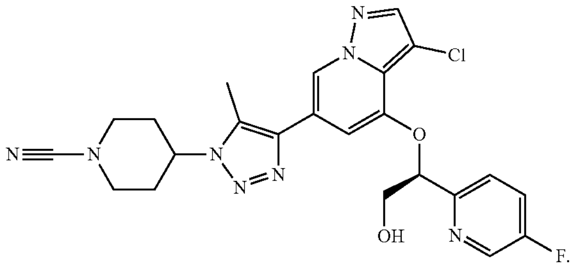 [SMILES: Cc1c(-c2cc(O[C@H](CO)c3ccc(F)cn3)c3c(Cl)cnn3c2)nnn1C1CCN(C#N)CC1]

WO/2022/187443 (International patent application number PCT/US2022/018644) and US2023/0095122 A1 (U.S. patent application Ser. No. 17/685,753) disclose how to make Examples 45 and 46.

Another FGFR3 inhibitor disclosed in WO/2022/187443 (International patent application number PCT/US2022/018644) and US2023/0095122 A1 (U.S. patent application Ser. No. 17/685,753) is 4-[4-[3-chloro-4-[2-hydroxy-1-(2-pyridyl)ethoxy]pyrazolo[1,5-a]pyridin-6-yl]-5-methyl-triazol-1-yl]piperidine-1-carbonitrile, Isomer 1, (hereinafter "Isomer A") which has the following structure:

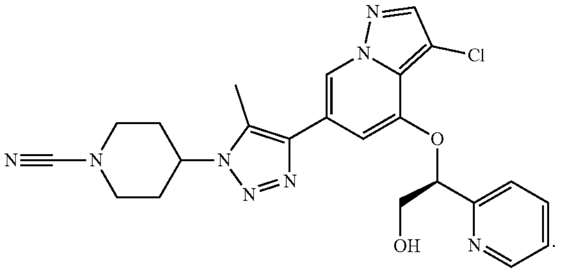 [SMILES: Cc1c(-c2cc(O[C@H](CO)c3ccccn3)c3c(Cl)cnn3c2)nnn1C1CCN(C#N)CC1]

This compound was disclosed as Example 151 in both PCT/US/2022/018644 and U.S. patent application Ser. No. 17/685,753. WO/2022/187443 (International patent application number PCT/US2022/018644) and US2023/0095122 A1 (U.S. patent application Ser. No. 17/685,753) disclose how to make Example 151.

Biological assays disclosed herein demonstrate that Isomers 1, 2, and A are FGFR3 inhibitors. The following assays demonstrate that certain compounds provided herein selectively target FGFR3.

FGFR3 and FGFR1 Enzyme Assay: FGFR3 protein was purchased from Reaction Biology (Cat. No. 1068), and FGFR1 protein was purchased from ThermoFisher Scientific (Cat. No. PV4105). Enzyme activity was monitored using the KinEASE™-TK Assay Kit (CisBio, Cat. No. 62TK0PEC) according to the manufacturer's instructions. All assays were performed at the respective KmATP for each kinase in KinEASE™ Kinase Buffer. Reactions were performed in a white, small volume polystyrene 384 well plate (Greiner, Cat. No. 784075-25).

An incubation was conducted with FGFR3 protein or FGFR1 protein, 125.0 nM TK-Biotin Substrate (CisBio), 7.81 nM Streptavidin-XL665 (CisBio), 0.25×Anti-Phosphorylate TK-Biotin-Cryptate (CisBio). Final enzyme concentrations were 0.25 nM in 10 uL reactions. Titration of Isomers 1, 2, and A were performed in a half-log manner in 100% dimethyl sulfoxide (DMSO) starting at 1 uM. Prior to the initiation of the reaction by adenosine triphosphate (ATP), FGFR1 protein and Isomers 1, 2, and A were pre-incubated for 15 minutes at room temperature, and FGFR3 protein and Isomers 1, 2, and A were pre-incubated on ice for 15 minutes. Reactions proceeded for 30 min at 30° C. Plates were quenched by the addition of the Anti-TK cryptate antibody/Streptavidin-XL665 mixture. After 1 hour. in the stopping solution, the plates were read on the Envision plate reader ((Perkin Elmer) (Ex. Filter. 320 nm and Em1 665 nm/Em2 615 nm)).

Ratios were converted to a percent of control (POC) using a ratiometric emission factor. One hundred POC was determined using no test compound, and 0 POC was determined in the presence of 1 uM of an appropriate control inhibitor. A 4-parameter logistic curve was fit to the POC values as a function of the concentration of Isomers 1, 2, and A, and the $IC_{50}$ value was the point where the best fit curve crossed 50 POC.

In the above assays Isomers 1, 2, and A each exhibited $IC_{50}$ values of less than 350 nM for FGFR3. In the above assays Isomers 2 and A exhibited $IC_{50}$ values of less than 100 nM for FGFR3 and were at least 3 fold more selective for FGFR3 than for FGFR1. In the above assays Isomers 2 and A exhibited $IC_{50}$ values of less than 50 nM for FGFR3 and were at least 10 fold more selective for FGFR3 than for FGFR1.

New cocrystalline forms of the above identified FGFR3 inhibitors are disclosed herein. These forms exhibit improved solid state and chemical stability over current forms of FGFR3 inhibitors, such as SDD forms of a FGFR3 inhibitor. They could be included in a pharmaceutical formulation, which would be expected to exhibit superior stability, relative to previously known, non-cocrystalline forms. Accordingly, described herein are cocrystalline forms of the above FGFR3 inhibitors and pharmaceutical compositions thereof.

Isomer 2 Forms

Disclosed herein is a cocrystalline form that comprises Isomer 2 and gallic acid coformer. Gallic acid, also known as 3,4,5-trihydroxybenzoic acid, has the structure illustrated below:

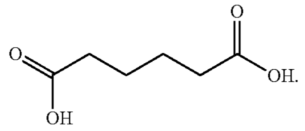

In one embodiment, gallic acid may have a variable water content between anhydrous and gallic acid mono-hydrate. In one embodiment, gallic acid is anhydrous gallic acid. In one embodiment, gallic acid is gallic acid mono-hydrate.

In one embodiment, THE may have a variable water content. In one embodiment, THF is anhydrous THF. In one embodiment, THE is wet THF. In one embodiment, THE may contain some water. In one embodiment, water is added to THF.

In an embodiment, the cocrystalline form has a ratio of Isomer 2 to gallic acid of about 2:1.

In an embodiment, the cocrystalline form further comprises a solvent. In an embodiment, the solvent is water and the cocrystalline form is a hydrate. In an embodiment, the cocrystalline form has a hemihydrate (herein referred to as "the cocrystalline form of Formula I"). In one embodiment, the cocrystalline form of Formula I is (Formula I)

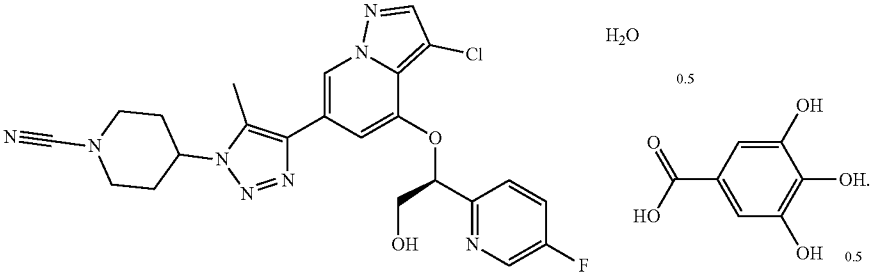

In one embodiment, the cocrystalline form of Formula I has variable water content. In one embodiment, the cocrystalline form of Formula I has water content ranging from about 0% to about 3.2% by thermogravimetric analysis (TGA).

In an embodiment, the cocrystalline form is a form after water loss of the cocrystalline form of Formula I, a "dehydrated hydrate". In one embodiment, the cocrystalline form of Formula I is dehydrated (herein referred to as "the cocrystalline form of Formula II"). In one embodiment, the cocrystalline form of Formula II is (Formula II)

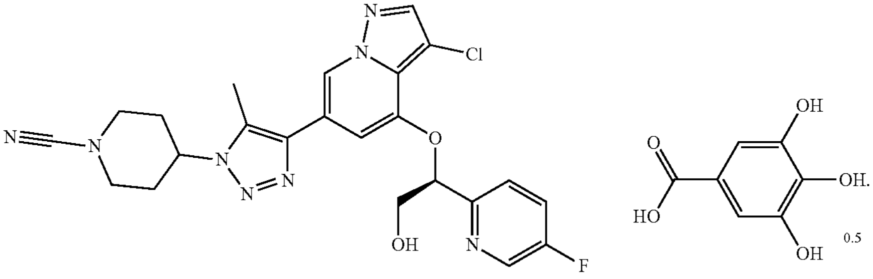

Disclosed herein is a cocrystalline form comprising Isomer 2 and Mono-Gallate coformer. In an embodiment, the cocrystalline form has a ratio of Isomer 2 to gallic acid about 1:1 (herein referred to as "the cocrystalline form of Formula III").

In one embodiment, the cocrystalline form of Formula III is (Formula III)

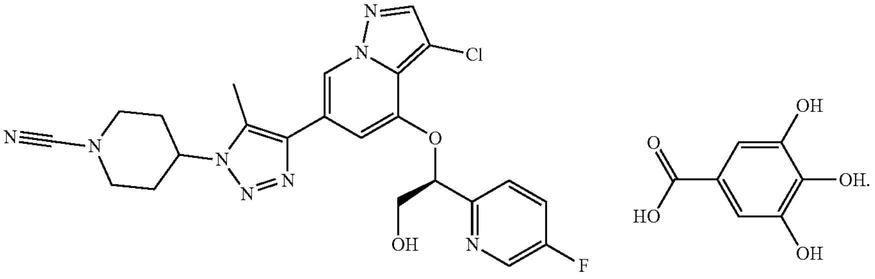

In an embodiment, the cocrystalline form of Formula III has a solvent. In an embodiment, the solvent is acetonitrile. In an embodiment, the cocrystalline form of Formula III has a mono-acetonitrile solvent (herein referred to as "the cocrystalline form of Formula IV"). In one embodiment, the cocrystalline form of Formula IV is (Formula IV)

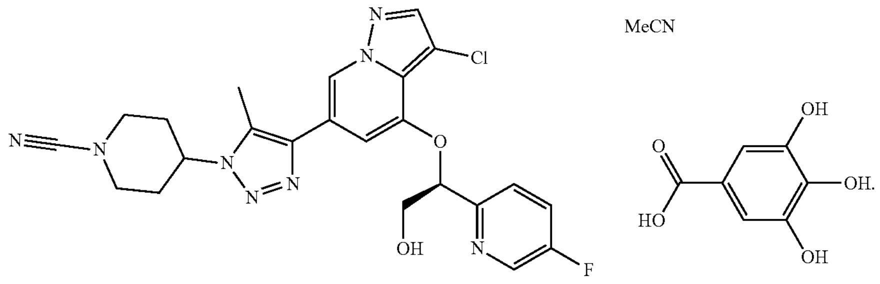

Isomer A Forms

Disclosed herein is a cocrystalline form of Isomer A and gallic acid coformer. In one embodiment, a cocrystalline form comprises Isomer A and Mono-Gallate coformer. In one embodiment, the cocrystalline form of Formula V ratio of Isomer A to gallic acid is about 1:1 (herein referred to as "the cocrystalline form of Formula V"). In one embodiment, the cocrystalline form of Formula V is (Formula V)

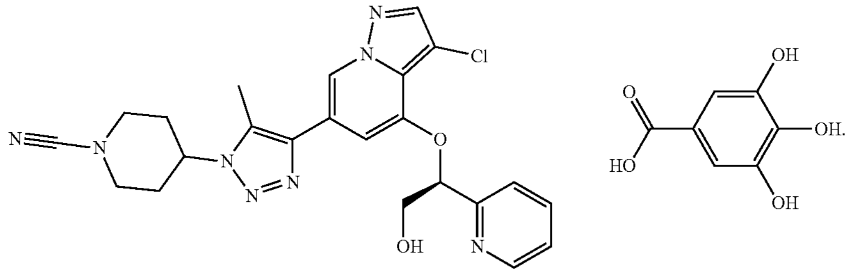

Disclosed herein is a cocrystalline form of Isomer A and nicotinamide coformer. Nicotinamide, also known as pyridine-3-carboxamide, has the structure illustrated below:

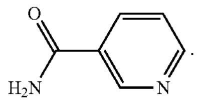

In one embodiment, a cocrystalline form comprises Isomer A and mono-nicotinamide coformer. In one embodiment, the ratio of Isomer A to nicotinamide is about 1:1 (herein referred to as "the cocrystalline form of Formula VI"). In one embodiment, the cocrystalline form of Formula VI is (Formula VI)

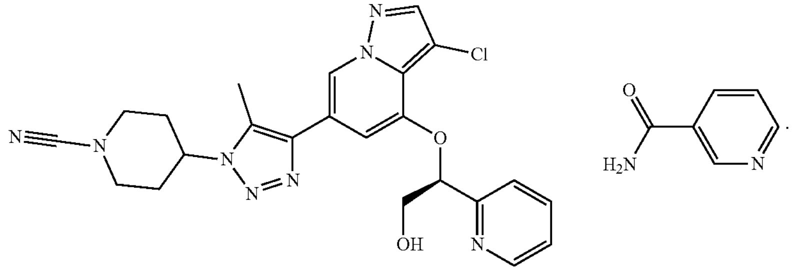

Also disclosed are pharmaceutical compositions comprising the above identified cocrystalline forms, methods of using the cocrystalline forms to treat conditions treatable by the inhibition of FGFR3, and methods of synthesizing the cocrystalline forms.

Accordingly, described herein are cocrystalline forms of FGFR3 and pharmaceutical compositions thereof. Preferably, the pharmaceutical composition further comprises a pharmaceutically acceptable carrier, diluent or excipient. Further described is a pharmaceutical composition comprising a cocrystalline form and further comprising a pharmaceutically acceptable carrier, diluent or excipient. Further described is the pharmaceutical composition wherein the composition contains at least about 80% by wt. of any of the cocrystalline forms. Further described is the pharmaceutical composition wherein the composition contains at least about 90% by wt. of any of the cocrystalline forms. Further described is the pharmaceutical composition wherein the composition contains at least about 95% by wt. of any of the cocrystalline forms.

In one embodiment, the pharmaceutical composition is for use in therapy. In another embodiment, disclosed herein is the use of the cocrystalline form of Formulae I, II, V, or VI, in therapy to treat a disease that is selected from the group consisting of systemic sclerosis, fibrosis, pulmonary fibrosis, achondroplasia, thanatophoric dysplasia, severe achondroplasia with developmental delay and acanthosis nigricans (SADDAN), muenke syndrome, and cancer.

Disclosed herein is a method of treating a FGFR3-associated cancer comprising administering to a patient in need thereof an effective amount of the cocrystalline form of Formulae I, II, V, or VI:

(Formula I)

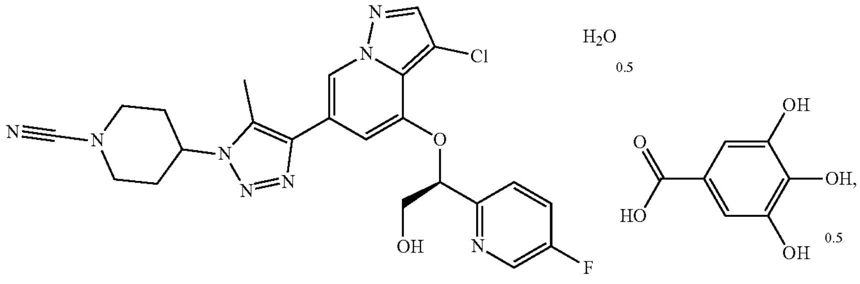

(Formula II)

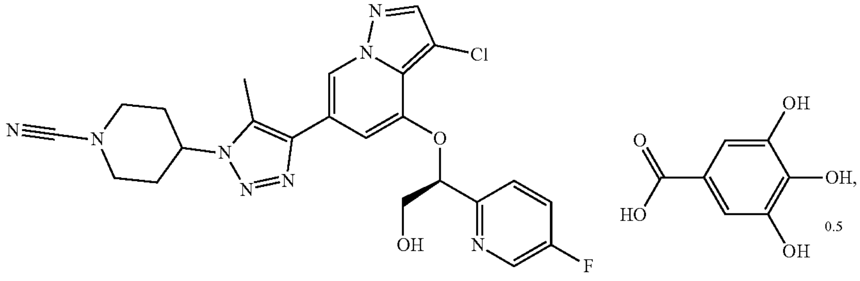

(Formula V)

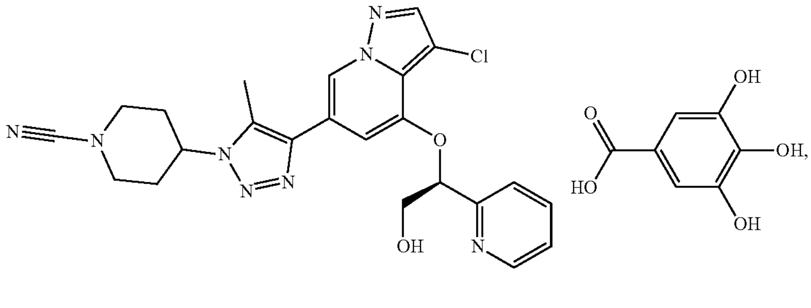

or

-continued (Formula VI)

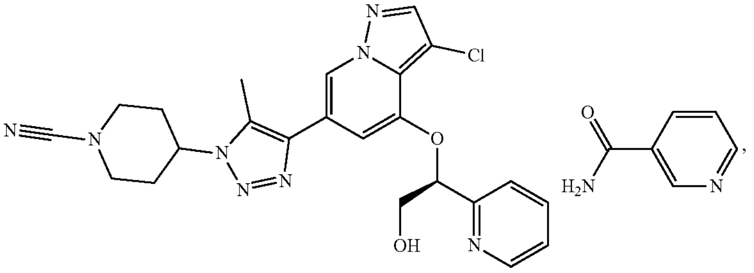

or pharmaceutical compositions thereof.

In one embodiment, a method of treating a FGFR3-associated cancer comprises administering to a patient in need thereof an effective amount of the cocrystalline form of Formulae I, II, V, or VI, or pharmaceutical compositions thereof.

In an aspect, disclosed herein is a cocrystalline form of Formulae I, II, V, or VI:

(Formula I)

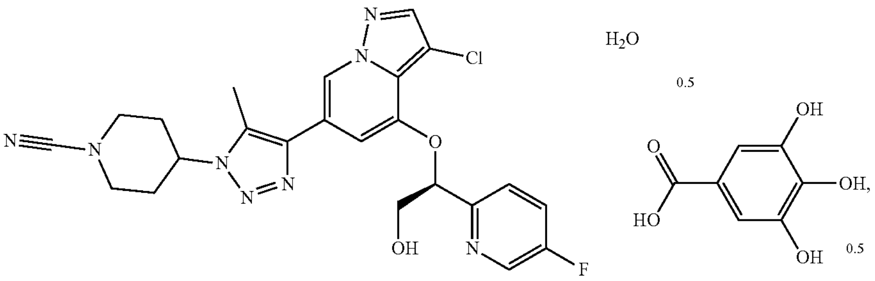

(Formula II)

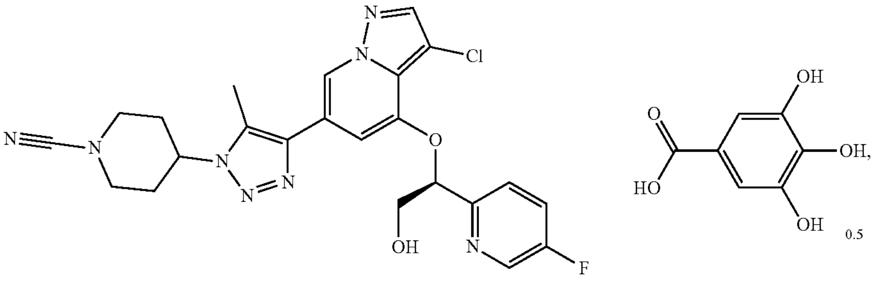

(Formula V)

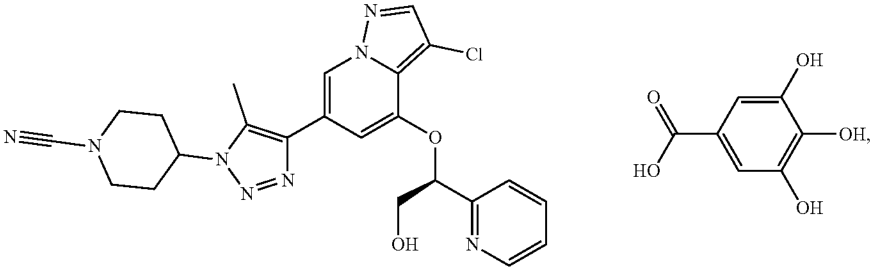

or

-continued (Formula VI)

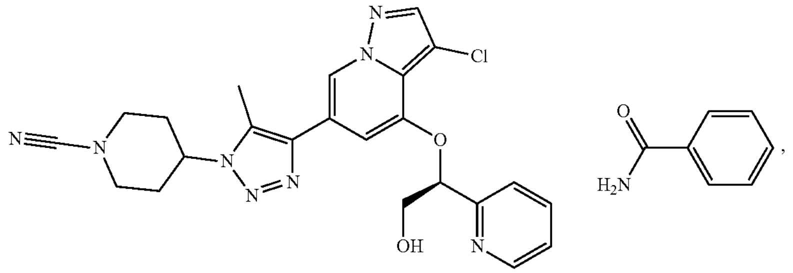

for use in treatment of a FGFR3-associated cancer.

In one embodiment, the cocrystalline form of Formulae I, II, V, or VI, for use in treatment of a FGFR3-associated cancer, wherein the FGFR3-associated cancer is non-muscle invasive bladder cancer.

In one embodiment, the cocrystalline form of Formulae I, II, V, or VI, for use in treatment of a FGFR3-associated cancer, wherein the FGFR3-associated cancer is intermediate risk non-muscle invasive bladder cancer.

In one embodiment, the cocrystalline form of Formulae I, II, V, or VI, for use in treatment of a FGFR3-associated cancer, wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

In one embodiment, the cocrystalline form of Formulae I, II, V, or VI, for use in treatment of a FGFR3-associated cancer, wherein the FGFR3-associated cancer is high risk non-muscle invasive bladder cancer.

In an aspect, disclosed herein is the use of an effective amount of a cocrystalline form of Formulae I, II, V, or VI:

(Formula I)

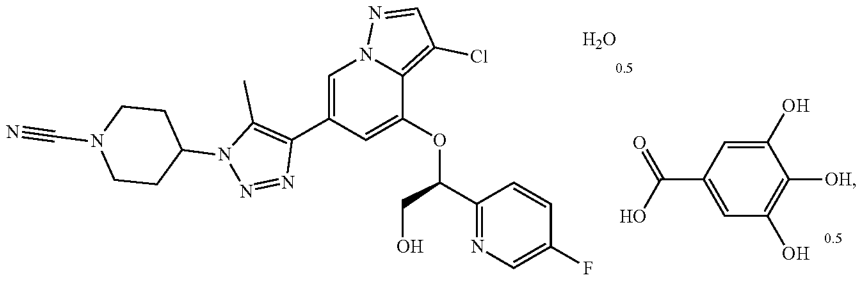

(Formula II)

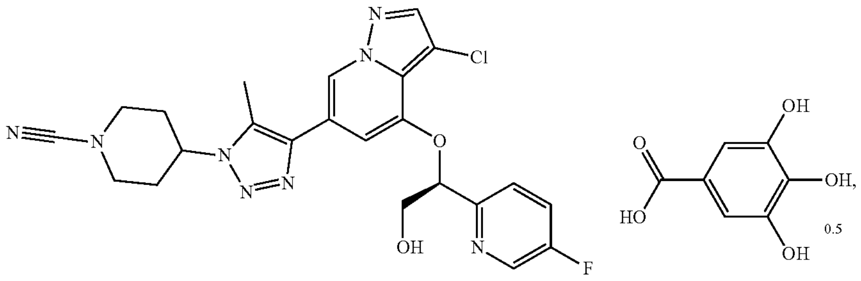

(Formula V)

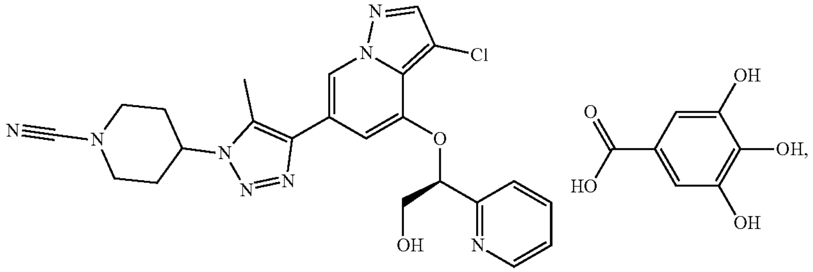

or

-continued (Formula VI)

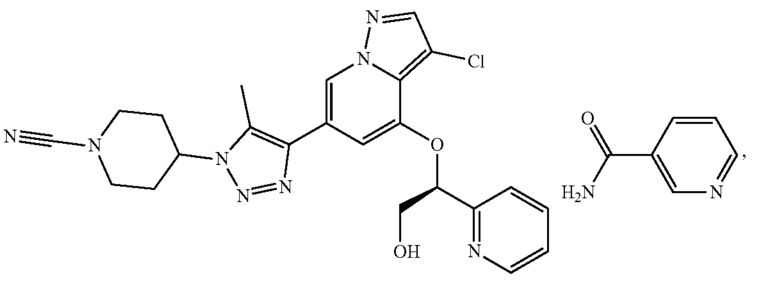

or pharmaceutical compositions thereof, in the manufacture of a medicament for treatment of a FGFR3-associated cancer.

In one embodiment, disclosed herein is the use of an effective amount of the cocrystalline form of Formulae I, II, V, or VI, or pharmaceutical compositions thereof in the manufacture of a medicament for treatment of a FGFR3-associated cancer, wherein the FGFR3-associated cancer is non-muscle invasive bladder cancer.

In one embodiment, disclosed herein is the use of an effective amount of the cocrystalline form of Formulae I, II, V, or VI, or pharmaceutical compositions thereof in the manufacture of a medicament for treatment of a FGFR3-associated cancer, wherein the FGFR3-associated cancer is intermediate risk non-muscle invasive bladder cancer.

In one embodiment, disclosed herein is the use of an effective amount of the cocrystalline form of Formulae I, II, V, or VI, or pharmaceutical compositions thereof in the manufacture of a medicament for treatment of a FGFR3-associated cancer, wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

In one embodiment, disclosed herein is the use of an effective amount of the cocrystalline form of Formulae I, II, V, or VI, or pharmaceutical compositions thereof in the manufacture of a medicament for treatment of a FGFR3-associated cancer, wherein the FGFR3-associated cancer is high risk non-muscle invasive bladder cancer.

In another aspect, disclosed herein is a process for the preparation of the cocrystalline form of Formula I comprising adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 and gallic acid to a solvent to give a slurry, adding cyclopentyl methyl ether to the slurry to form a white precipitate. In an embodiment, the process for the preparation of the cocrystalline form of Formula I further comprises seeding the slurry with the cocrystalline form of Formula I.

Disclosed herein is a process for preparing the cocrystalline form of Formula II comprising the step of heating the cocrystalline form of Formula I.

Disclosed herein is a process for the preparation of the cocrystalline form of Formula IV comprising the step of combining the cocrystalline form of Formula I with acetonitrile.

Disclosed herein is a process for the preparation of the cocrystalline form of Formula V comprising the step of adding gallic acid to Isomer A dissolved in ethyl acetate.

Disclosed herein is a process for the preparation of the cocrystalline form of Formula VI comprising the step of dissolving Isomer A in ethyl acetate saturated with nicotinamide.

DETAILED DESCRIPTION

In one embodiment, the cocrystalline form of Formula I has variable water content. In one embodiment, the cocrystalline form of Formula I has water content ranging from about 0% to about 3.2%.

In one embodiment, the cocrystalline form of Formula I and the cocrystalline form of Formula II are each characterized by having an x-ray powder diffraction (XRPD) pattern using CuKα radiation comprising a peak at 8.4° and one or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and four or more peaks at 6.7°, 9.2°, 10.0°, 13.4°, 14.10, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and five or more peaks at 6.7°, 9.2°, 10.0°, 13.4°, 14.10, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and six or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and seven or more peaks at 6.7°, 9.2°, 10.0°, 13.4°, 14.10, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and eight or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and nine or more peaks at 6.7°, 9.2°, 10.0°, 13.4°, 14.10, 15.6°, 16.9°, 18.4°, 19.6°, 21.3°, 23.4°, or 24.2° with a tolerance for the diffraction angles of ±0.2 degrees. In one embodiment, the cocrystalline form of Formula I and the cocrystalline form of Formula II are each characterized by having an x-ray powder diffraction (XRPD) pattern using CuKα radiation comprising a peak at 8.4° and ten or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees.

In one embodiment, the cocrystalline form of Formula I and the cocrystalline form of Formula II are each characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4°; with a tolerance for the diffraction angles of ±0.2 degrees. In one embodiment, the cocrystalline form of Formula I and the cocrystalline form of Formula II are each characterized by an XRPD pattern using CuKα radiation having a diffraction peak at diffraction angle 2-theta of 8.4° in combination with two or more of the peaks selected from the group consisting of 15.6°, 21.3°, 6.7°, and 23.4°; with a tolerance for the diffraction angles of ±0.2 degrees. In one embodiment, the cocrystalline form of Formula I and the cocrystalline form of Formula II are each characterized by an XRPD pattern using CuKα radiation having a diffraction peak at diffraction angle 2-theta of 8.4° in combination with three or more of the peaks selected from the group consisting of 15.6°, 21.3°, 6.7°, and 23.4°; with a tolerance for the diffraction angles of ±0.2 degrees.

In one embodiment, the cocrystalline form of Formula I and the cocrystalline form of Formula II are each characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4°; and in combination with one or more peaks at 9.2°, 10.0°, 13.4°, 14.10, 16.9°, 18.4°, 19.6°, or 24.2° with a tolerance for the diffraction angles of ±0.2 degrees. In one embodiment, the diffraction peak at diffraction angle 2-theta of 8.4° is intense. In one embodiment, one or more peaks at diffraction angle 2-theta selected from the group consisting of 15.6°, 21.3°, 6.7°, and 23.4° are intense. In one embodiment, one or more peaks at diffraction angle 2-theta selected from the group consisting of 15.6° and 21.3° are intense.

In one embodiment, the cocrystalline form of Formula I and the cocrystalline form of Formula II are characterized by a $^{13}C$ solid state NMR spectrum comprising peaks referenced to the carbonyl resonance of glycine (δ=176.5 ppm) at: 8.1, 11.1, 26.6, 28.2, 32.3, 35.0, 80.7, 81.7, 99.6, 102.3, 110.9, 158.0, 160.0, 168.2, 175.0 ppm, with a tolerance of ±0.2 ppm.

In one embodiment, the cocrystalline form of Formula IV is characterized by having an XRPD (XRPD) pattern using CuKα radiation comprising a peak at 14.6° and one or more peaks at 5.7°, 6.5°, 9.8°, 13.0°, 13.5°, 16.5°, 17.10, 18.9°, 19.7°, 23.8°, or 24.5° with a tolerance for the diffraction angles of ±0.2 degrees. In one embodiment, the cocrystalline form of Formula IV is characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7°; with a tolerance for the diffraction angles of ±0.2 degrees. In one embodiment, the cocrystalline form of Formula IV is characterized by an XRPD pattern using CuKα radiation having a diffraction peak at diffraction angle 2-theta of 14.6° in combination with two or more of the peaks selected from the group consisting of 9.8°, 23.8°, 6.5°, and 19.7°; with a tolerance for the diffraction angles of ±0.2 degrees. In one embodiment, the cocrystalline form of Formula IV is characterized by an XRPD pattern using CuKα radiation having a diffraction peak at diffraction angle 2-theta of 14.6° in combination with three or more of the peaks selected from the group consisting of 9.8°, 23.8°, 6.5°, and 19.7°; with a tolerance for the diffraction angles of ±0.2 degrees.

In one embodiment, the cocrystalline form of Formula IV is characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7°; and in combination with one or more peaks at 5.7°, 6.5°, 9.8°, 13.0°, 13.5°, 16.5°, 17.10, 18.9°, 19.7°, 23.8°, or 24.5° with a tolerance for the diffraction angles of ±0.2 degrees. In one embodiment, the diffraction peak at diffraction angle 2-theta of 14.6° is intense. In one embodiment, one or more peaks at diffraction angle 2-theta selected from the group consisting of 9.8°, 23.8°, 6.5°, and 19.7° are intense. In one embodiment, one or more peaks at diffraction angle 2-theta selected from the group consisting of 9.8° and 23.8° are intense.

In one embodiment, the cocrystalline form of Formula V is characterized by having an XRPD pattern using CuKα radiation comprising a peak at 6.9° and one or more peaks at 9.1°, 10.5°, 12.7°, 15.7°, 16.3°, 16.8°, 17.1°, 17.9°, 18.4°, 21.0°, or 23.4°, with a tolerance of ±0.2 ppm. In one embodiment, the cocrystalline form of Formula V is characterized by an XRPD pattern using CuKα radiation having a diffraction peak at diffraction angle 2-theta of 6.9° in combination with one or more of the peaks selected from the group consisting of 12.7°, 18.4°, 9.10, and 23.4°; with a tolerance for the diffraction angles of ±0.2 degrees. In one embodiment, the cocrystalline form of Formula V is characterized by an XRPD pattern using CuKα radiation having a diffraction peak at diffraction angle 2-theta of 6.9° in combination with two or more of the peaks selected from the group consisting of 12.7°, 18.4°, 9.10, and 23.4°; with a tolerance for the diffraction angles of ±0.2 degrees. In one embodiment, the cocrystalline form of Formula V is characterized by an XRPD pattern using CuKα radiation having a diffraction peak at diffraction angle 2-theta of 6.9° in combination with three or more of the peaks selected from the group consisting of 12.7°, 18.4°, 9.10, and 23.4°; with a tolerance for the diffraction angles of ±0.2 degrees.

In one embodiment, the cocrystalline form of Formula V is characterized by an XRPD pattern using CuKα radiation having a diffraction peak at diffraction angle 2-theta of 6.9° in combination with one or more of the peaks selected from the group consisting of 12.7°, 18.4°, 9.10, and 23.4°; in combination with one or more of the peaks selected from the group consisting of 10.5°, 15.7°, 16.3°, 16.8°, 17.10, 17.9°, 21.0°, and 23.4° with a tolerance for the diffraction angles of ±0.2 degrees.

In one embodiment, the cocrystalline form of Formula V diffraction peak at diffraction angle 2-theta of 6.9° is intense. In one embodiment, one or more peaks at diffraction angle 2-theta selected from the group consisting of 12.7°, 18.4°, 9.10, and 23.4° are intense. In one embodiment, the cocrystalline form of Formula V one or more peaks at diffraction angle 2-theta selected from the group consisting of 12.7° and 18.4° are intense.

In one embodiment, the cocrystalline form of Formula VI is characterized by having an XRPD pattern using CuKα radiation comprising a peak at 13.7° and one or more peaks at 6.8°, 8.2°, 9.6°, 12.3°, 15.8°, 17.5°, 17.9°, 18.7°, 19.0°, 22.2°, 22.9°, 24.7°, or 26.10, with a tolerance of ±0.2 ppm. In one embodiment, the cocrystalline form of Formula VI is characterized by an XRPD pattern using CuKα radiation having a diffraction peak at diffraction angle 2-theta of 13.7° in combination with one or more of the peaks selected from the group consisting of 9.6°, 17.9°, and 24.7°; with a tolerance for the diffraction angles of ±0.2 degrees. In one embodiment, the cocrystalline form of Formula VI is characterized by an XRPD pattern using CuKα radiation having a diffraction peak at diffraction angle 2-theta of 13.7° in combination with two or more of the peaks selected from the group consisting of 9.6°, 17.9°, and 24.7°; with a tolerance for the diffraction angles of ±0.2 degrees. In one embodiment, the cocrystalline form of Formula VI is characterized by an XRPD pattern using CuKα radiation having a diffraction peak at diffraction angle 2-theta of 13.7° in combination with the peaks selected from the group consisting of 9.6°, 17.9°, and 24.7°; with a tolerance for the diffraction angles of ±0.2 degrees.

In one embodiment, the cocrystalline form of Formula VI is characterized by an XRPD pattern using CuKα radiation having a diffraction peak at diffraction angle 2-theta of 13.7° in combination with one or more of the peaks selected from the group consisting of 9.6°, 17.9°, and 24.7°; in combination with one or more of the peaks selected from the group consisting of 6.8°, 8.2°, 12.3°, 15.8°, 17.5°, 18.7°, 19.0°, 22.2°, 22.9°, or 26.10 with a tolerance for the diffraction angles of ±0.2 degrees.

In one embodiment, the cocrystalline form of Formula VI diffraction peak at diffraction angle 2-theta of 13.7° is intense. In one embodiment, one or more peaks at diffraction angle 2-theta selected from the group consisting of 9.6°, 17.9°, and 24.7° are intense. In one embodiment, the cocrystalline form of Formula VI one or more peaks at diffraction angle 2-theta selected from the group consisting of 9.6° and 17.9° are intense.

Some cocrystalline forms may provide improved solubility over other cocrystalline forms or current formulations such as freebase or spray dry dispersions (SDD). For example, the cocrystalline form of Formula I may be about two to about five times, about three to about five times, or about four to about five times more soluble than a freebase form of Isomer 2. For example, the cocrystalline form of Formula I may be about four to about five times more soluble than a freebase form of Isomer 2, such as in fasted simulated intestinal fluid. For example, the cocrystalline form of Formula I may be about two to about three times more soluble than an Isomer 2 with IPMC SDD, such as in fasted simulated intestinal fluid. Some cocrystalline forms may enable oral administration of FGFR3 inhibitors in comparison to other cocrystalline forms or current formulations such as spray dry dispersions (SDD).

Some cocrystalline forms may be more stable than other cocrystalline forms or current formulations such as spray dry dispersions (SDD). For example, the crystalline form of Formula I is more stable at 40° C. and 75% relative humidity than multiple current SDD formulations including Isomer 2, such as Isomer 2 with IPMC SDD, Isomer 2 with HPMC-AS-M SDD, and Isomer 2 with PVP-VA SDD. Cocrystalline forms may be more stable than SDDs. Cocrystalline forms may have improved properties, such as less hygroscopicity. It is an aim of certain embodiments of the present disclosure to utilize cocrystalline forms which require less operational process steps than current formulations. Cocrystalline forms may result in fewer operational process steps which includes the benefits of simplification of the supply chain and fewer number of unit operations. Cocrystalline forms undergo less material transfers from different sites, such as transferring once to incorporate the co-crystal into a formulation, such as tablets, capsules, and suspensions. It is generally recognized that SDD formulations start with manufacturing the Active Pharmaceutical Ingredient (API) at a first site, transfer to a second site for incorporation of the API in the SDD, and then transfer to a third site for incorporation of the SDD with API into a formulation, such as tablets, capsules, and suspensions. Certain embodiments of the present disclosure utilize cocrystalline forms which require less solvent than current formulations leading to less environmental impact.

In one embodiment, the pharmaceutical composition is for use in treatment of a FGFR3-associated cancer. Examples of FGFR3-associated cancers include, but are not limited to breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer. In one embodiment, the FGFR3-associated cancer is urothelial cancer, bladder cancer, urothelial bladder cancer, advanced urothelial bladder cancer, metastatic urothelial bladder cancer, non-muscle invasive bladder cancer, or muscle invasive bladder cancer. In one embodiment, the FGFR3-associated cancer is urothelial cancer. In one embodiment, the FGFR3-associated cancer is bladder cancer. In one embodiment, the FGFR3-associated cancer is urothelial bladder cancer. In one embodiment, the FGFR3-associated cancer is advanced urothelial bladder cancer. In one embodiment, the FGFR3-associated cancer is metastatic urothelial bladder cancer. In one embodiment, the FGFR3-associated cancer is non-muscle invasive bladder cancer. In one embodiment, the FGFR3-associated cancer is intermediate risk non-muscle invasive bladder cancer. In one embodiment, the FGFR3-associated cancer is Bacillus Calmette-Guerin (BCG)-unresponsive non-muscle invasive bladder cancer. In one embodiment, the FGFR3-associated cancer is Bacillus Calmette-Guerin (BCG) recurrent non-muscle invasive bladder cancer. In one embodiment, the FGFR3-associated cancer is high risk non-muscle invasive bladder cancer. In one embodiment, the FGFR3-associated cancer is muscle invasive bladder cancer.

Definitions

Unless defined otherwise, all technical and scientific terms used herein have the meaning commonly understood by a person skilled in the art to which this disclosure belongs. As used herein, the following terms have the meanings ascribed to them below, unless specified otherwise.

As used herein, "cancer" refers to an FGFR3-associated cancer. The FGFR3-associated cancer may exhibit at least one of a point mutation/insertion/deletion and/or fusion. Examples of specific cancers that may be treated using the compounds disclosed herein include, but are not limited to breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer. Alternatively, the cancer is urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, or muscle invasive bladder cancer. In one embodiment, the FGFR3-associated cancer is urothelial cancer. In one embodiment, the FGFR3-associated cancer is bladder cancer. In one embodiment, the FGFR3-associated cancer is urothelial bladder cancer. In one embodiment, the FGFR3-associated cancer is advanced urothelial bladder cancer. In one embodiment, the FGFR3-associated cancer is metastatic urothelial bladder cancer. In one embodiment, the FGFR3-associated cancer is non-muscle invasive bladder cancer. In one embodiment, the FGFR3-associated cancer is intermediate risk non-muscle invasive bladder cancer. In one embodiment, the FGFR3-associated cancer is Bacillus Calmette-Guerin (BCG)-unresponsive non-muscle invasive bladder cancer. In one embodiment, the FGFR3-associated cancer is Bacillus Calmette-Guerin (BCG) recurrent non-muscle invasive bladder cancer. In one embodiment, the FGFR3-associated cancer is high risk non-muscle invasive bladder cancer. In one embodiment, the FGFR3-associated cancer is muscle invasive bladder cancer.

The terms "NMIBC" or "non-muscle invasive bladder cancer" mean bladder cancer staged as T0, Ta, T1, or CIS according to the Tumor, Node, Metastasis Classification (TNM). The term "TO" means the first stage of disease where there is no evidence of primary tumor according to the Tumor, Node, Metastasis Classification (TNM). The terms "Ta", "T1", "T2", "T3", and "T4" mean the size or extent of the primary tumor according to the Tumor, Node, Metastasis Classification (TNM).

The terms "intermediate risk non-muscle invasive bladder cancer", "intermediate risk NMIBC", or "IR NMIBC" mean multiple or recurrent low-grade Ta tumors. The following factors to be considered are number of tumors such as greater than one, size of tumors such as greater than 3 cm, timing such as recurrence within 1 year, frequency of recurrences such as greater than one recurrence per year, and previous treatment.

The terms "high risk non-muscle invasive bladder cancer", "high risk NMIBC", or "HR NMIBC" mean recurrent, bacillus Calmette-Guerin (BCG) unresponsive, high-grade, T1 or CIS tumors wherein recurrence can be after BCG therapy. The following factors to be considered are tumor grade, size of tumors such as greater than 3 cm, timing such as recurrence within 1 year, frequency of recurrences such as greater than one recurrence per year, and previous treatment.

The terms "treatment," "treat," "treating," and the like, are meant to include slowing, stopping, or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed, stopped, or reversed.

"Effective amount" means the amount of the cocrystalline form (the cocrystalline form of Formulae I, II, V, or VI) that will elicit the biological or medical response of or desired therapeutic effect on a patient by a treating clinician.

As used herein, "patient" refers to a mammal and more preferably, to a human.

An effective amount can be determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

In some embodiments, "cocrystalline" refers to solids that are crystalline materials composed of two or more different molecular compounds generally in a stoichiometric ratio. A broader definition is that cocrystals comprise two or more components that form a unique crystalline structure having unique properties. A cocrystalline hydrate refers to a crystalline material composed of two or more different molecular compounds generally in a stoichiometric ratio along with water. The amount of water may be in a stoichiometric ratio but may also be non-stoichiometric. Removal of the water from the crystal may or may not disrupt the lattice and is in general referred to as a dehydrated hydrate. Hydrates are known in the art (See e.g. Polymorphism in the Pharmaceutical Industry: Solid Form and Drug Development Chapter 6; Hygroscopicity and Hydrates in Pharmaceutical Solids (Rolf Hilfiker, Markus von Raumer, editors, John Wiley & Sons, 2018)).

Each cocrystalline form (the cocrystalline form of Formula I, Formula II, Formula IV, Formula V, or Formula VI) is preferably formulated as pharmaceutical compositions administered by any route which makes the compound bioavailable, including oral, intravenous, and transdermal routes. Most preferably, such compositions are for oral administration. Such pharmaceutical compositions and processes for preparing same are known in the art. (See, e.g., Remington: The Science and Practice of Pharmacy (D. B. Troy, Editor, $21^{st}$ Edition, Lippincott, Williams & Wilkins, 2006).

The term "intense" is defined herein as detected signal from the sample greater than background signal from the instrument.

To provide a more concise description, some of the quantitative expressions herein are recited as a range from about amount X to about amount Y. It is understood that when a range is recited, the range is not limited to the recited upper and lower bounds, but rather includes the full range from about amount X through about amount Y, or any range therein.

"Room temperature" or "RT" refers to the ambient temperature of a typical laboratory, which is typically around 25° C.

In some embodiments, the term "excipient" refers to any substance needed to formulate the composition to a desired form. For example, suitable excipients include but are not limited to, diluents or fillers, binders or granulating agents or adhesives, disintegrants, lubricants, antiadherents, glidants, dispersing or wetting agents, dissolution retardants or enhancers, adsorbents, buffers, chelating agents, preservatives, colors, flavors and sweeteners.

A "pharmaceutically acceptable carrier, diluent, or excipient" is a medium generally accepted in the art for the delivery of biologically active agents to mammals, e.g., humans. The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various excipients, such as are commonly used in the art, can be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); Goodman and Gilman's: The Pharmacological Basis of Therapeutics, $12^{th}$ Ed., The McGraw-Hill Companies.

In some embodiments, the singular forms "a," "an," and "the" include plural referents unless the context clearly dictates otherwise.

In some embodiments, ranges and amounts can be expressed as "about" a particular value or range. About also includes the exact amount. Hence, "about 5 grams" means "about 5 grams" and also "5 grams." It also is understood that ranges expressed herein include whole numbers within the ranges and fractions thereof. For example, a range of between 5 grams and 20 grams includes whole number values such as 5, 6, 7, 8, 9, 10, 11, 12, 13, 14, 15, 16, 17, 18, 19 and 20 grams, and fractions within the range including, but not limited to, 5.25, 6.5, 8.75 and 11.95 grams.

In some embodiments, "optional" or "optionally" means that the subsequently described event or circumstance does or does not occur and that the description includes instances where said event or circumstance occurs and instances where it does not. For example, a reaction mixture that "optionally includes a catalyst" means that the reaction mixture contains a catalyst or it does not contain a catalyst.

In some embodiments, "relative intensity" means the percentage of any peak in relation to the highest peak in the relevant spectrum.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

All combinations of the embodiments pertaining to the aspects described herein are specifically embraced by the present disclosure just as if each and every combination was individually explicitly recited, to the extent that such combinations embrace possible aspects. In addition, all sub-combinations of the embodiments contained within the aspects described herein, as well as all sub-combinations of the embodiments contained within all other aspects described herein, are also specifically embraced by the present disclosure just as if each and every sub-combination of all embodiments are explicitly recited herein.

EXAMPLES

The following examples further illustrate the disclosure.

The XRPD patterns of Examples 1-3 were obtained on a Bruker D8 Endeavor X-ray powder diffractometer, equipped with a CuKα (1.5418 Å) source and a Linxeye detector, operating at 40 kV and 40 mA. The samples are scanned between 4 and 42 2θ°, with a step size of 0.009 2θ° and a scan rate of 0.5 seconds/step, and using 0.3° primary slit opening, and 3.9° PSD opening. The dry powder is packed on a quartz or silicon sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the forms are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Solid state NMR is obtained on an Agilent DD2-400 spectrometer (100.6 MHz). The sample is packed into a 4 mm PENCIL type silicon nitride rotor and rotated at 12 kHz at the magic angle. The spectrum is acquired at ambient temperature with phase modulated (SPINAL-64) high power $^{1}H$ decoupling during the acquisition time, a ramped amplitude cross polarization contact time of 5 ms, a 30 ms acquisition time, a 10 second delay between scans, a spectral width of 45 kHz with 2678 data points, and 1600 co-added scans. The free induction decay (FID) is processed using Agilent VnmrJ 3.2A software with 65536 points and an exponential line broadening factor of 10 Hz to improve the signal-to-noise ratio. The first three data points of the FID are back predicted using the VNMR linear prediction algorithm to produce a flat baseline. The chemical shifts of the spectral peaks are externally referenced to the carbonyl carbon resonance of glycine at 176.5 ppm.

Dynamic vapor sorption (DVS) analysis is obtained at 25° C. using a TA Instruments Q5000SA VTI flow moisture balance running TA Thermal Advantage, v5.2.6 and Universal Analysis 2000, v4.5a Software. The equilibrium criterion was <0.01% weight change in 5 minutes for a maximum of 60 minutes. Humidity verification calibration was performed with sodium bromide. The weight calibration was performed with manufacturer-supplied standards.

Differential scanning calorimetry (DSC) analysis is obtained using a TA Q2000 DSC run by TA Thermal Advantage Software v5.2.6 and data analyzed by Universal Analysis 2000 v4.5a. Samples were equilibrated at 25° C. in crimped aluminum pans and heated to 300° C. at 10° C./min with a 50 mL/min nitrogen purge. The temperature and heat flow were calibrated against indium melting.

Thermogravimetric analysis (TGA) is obtained using a TA Instruments Q5000 TGA run by TA Thermal Advantage Software v5.2.6 and data analyzed by Universal Analysis 2000 v4.5a. Samples were heated from ambient temperature (approximately 25° C.) to 200° C. at a rate of 10° C./min. Nitrogen was the carrier (10 mL/min) and purge (50 mL/min) gas. Temperature was calibrated by Curie temperature determination with nickel and alumel standards. The weight calibration was performed with manufacturer-supplied standards.

Example 1

4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2, Hemi-Gallic Acid Cocrystalline Form, Hemihydrate ("the Cocrystalline Form of Formula I")

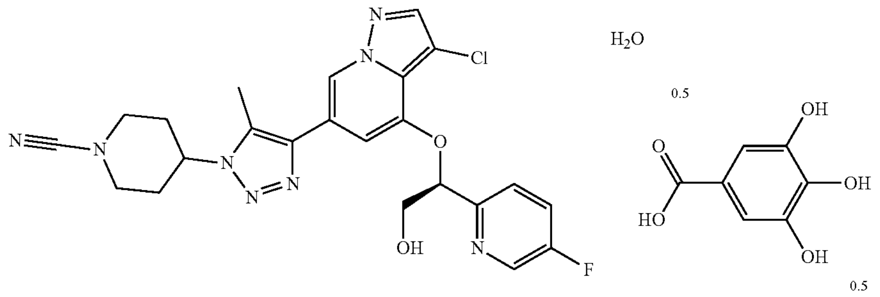

4-[4-[3-Chloro-4-[1-(5-fluoro-2-pyridyl)-2-hydroxy-ethoxy]pyrazolo[1,5-a]pyridin-6-yl]-5-methyl-triazol-1-yl] piperidine-1-carbonitrile, Isomer 2 (2.25 g) and gallic acid (0.69 g) are suspended in THE (10.4 mL). The slurry is heated to 50° C. while stirring at 200 rpm; all solids dissolve. The solution is cooled to 25° C., the stirring rate is increased to 400 rpm and cyclopentyl methyl ether (30 mL) is added at a rate of 0.04 mL/min (over −12 hours) during which time a white precipitate is formed. After overnight stirring at 25° C., the solid product is isolated by vacuum filtration onto a medium-pore fritted filter. The wetcake is washed with cyclopentyl methyl ether (5 mL) and dried at 50° C. under vacuum. The title compound is produced in 86% yield (2.25 g).

4-[4-[3-Chloro-4-[1-(5-fluoro-2-pyridyl)-2-hydroxy-ethoxy]pyrazolo[1,5-a]pyridin-6-yl]-5-methyl-triazol-1-yl] piperidine-1-carbonitrile, Isomer 2 (7.0 g) and gallic acid (2.64 g) are suspended in THE (33.2 mL). The slurry is heated to 50° C.; all solids dissolve. The solution is cooled to 25° C. and seeded with 415 mg of hemi-gallic acid hemihydrate cocrystal. The thin slurry is aged for 25 minutes at 25° C., then cyclopentyl methyl ether (77.5 mL) is added at a rate of 0.11 mL/min during which time a thick off-white slurry is formed. After overnight stirring at 25° C., the solid product is isolated by vacuum filtration onto a medium-pore fritted filter. The wetcake is washed with cyclopentyl methyl ether (16.5 mL) and dried at 50° C. under vacuum. The title compound is produced in 89% yield (7.38 g). $^{13}C$ Solid state NMR (101 MHz) for the cocrystalline form of Formula I includes peaks at δ 8.1, 11.1, 26.6, 28.2, 32.3, 35.0, 80.7, 81.7, 99.6, 102.3, 110.9, 158.0, 160.0, 168.2, 175.0.

XRPD of 4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2, Hemi-Gallic Acid Cocrystalline Form ("the Cocrystalline Form of Formula I")

A prepared sample of the cocrystalline form of Formula I is characterized by an XRPD pattern using CuKα radiation as having diffraction peaks (2-theta values) as described in Table 1 below, and in particular having a peak at 8.4 in combination with one or more of the peaks selected from the group consisting of 15.6, 21.3, 6.7, and 23.4; with a tolerance for the diffraction angles of ±0.2 degrees.

TABLE 1

XRPD peaks of Example 1

| Peak | Angle (°2-Theta) +/−0.2° | Relative Intensity (% of most intense peak) |
|---|---|---|
| 1 | 6.7 | 73.1 |
| 2 | 8.4 | 100 |
| 3 | 9.2 | 24.0 |
| 4 | 10.0 | 13.5 |
| 5 | 13.4 | 43.4 |
| 6 | 14.1 | 50.9 |
| 7 | 15.6 | 60.7 |
| 8 | 16.9 | 32.0 |
| 9 | 18.4 | 48.6 |
| 10 | 19.6 | 60.1 |
| 11 | 21.3 | 81.0 |
| 12 | 23.4 | 76.9 |
| 13 | 24.2 | 57.9 |

The cocrystalline form of Formula I presented as acicular (needle morphology) when examined by polarized light microscopy.

A prepared sample of the cocrystalline form of Formula I is characterized by dynamic vapor sorption as having a range of water content from about 1% at 0% RH to about 3.2% at 90% RH.

Example 1A

4-[4-[3-Chloro-4-[1-(5-fluoro-2-pyridyl)-2-hydroxy-ethoxy]pyrazolo[1,5-a]pyridin-6-yl]-5-methyl-tri-azol-1-yl]piperidine-1-carbonitrile, Isomer 2, Hemi-Gallic Acid Cocrystalline Form, Dehydrated Hydrate ("the Cocrystalline Form of Formula II")

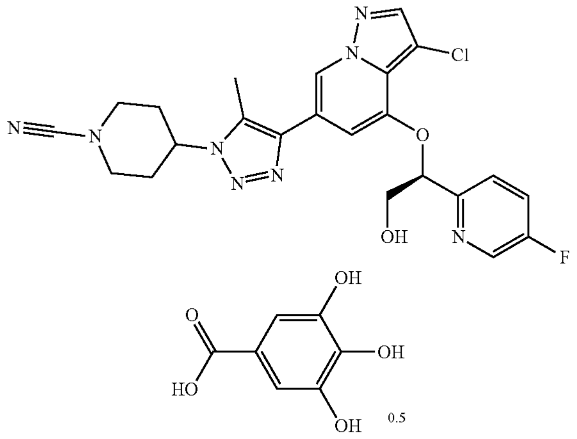

A prepared sample of the cocrystalline form of Formula I is characterized by thermogravimetric analysis as having a step change due to water loss of about 1.7% prior to the melt of the cocrystalline form of Formula II.

Example 2

4-[4-[3-Chloro-4-[1-(5-fluoro-2-pyridyl)-2-hydroxy-ethoxy]pyrazolo[1,5-a]pyridin-6-yl]-5-methyl-tri-azol-1-yl]piperidine-1-carbonitrile, Isomer 2, Mono-Gallic Acid Cocrystalline Form, Monoacetonitrile ("the Cocrystalline Form of Formula IV")

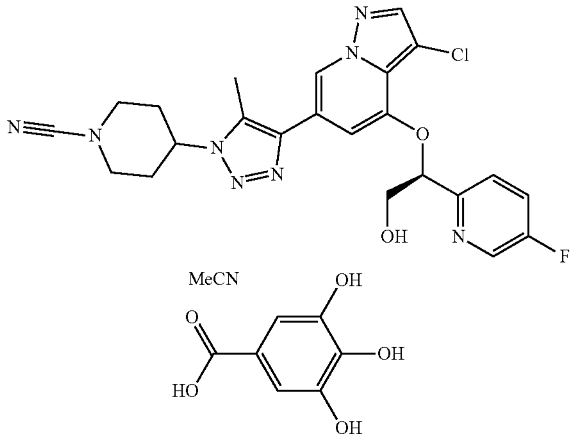

The cocrystalline form of Formula I (285 mg) is combined with acetonitrile (4 mL) and stirred at ambient temperature overnight. A thick white slurry is formed, which is transferred to a centrifuge tube filter (5 mL Centrex MF-5.0, 0.45 µm, nylon) and is centrifuged (330 rpm) at ambient temperature for 5 minutes. The resulting solid is air dried to give the title compound.

XRPD of 4-[4-[3-chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2, Mono-Gallic Acid Cocrystalline Form ("the Cocrystalline Form of Formula IV")

A prepared sample of the cocrystalline form of Formula IV is characterized by an XRPD pattern using CuKα radiation as having diffraction peaks (2-theta values) as described in Table 2 below, and in particular having a peak at 14.6 in combination with one or more of the peaks selected from the group consisting of 9.8, 23.8, 6.5, and 19.7; with a tolerance for the diffraction angles of ±0.2 degrees.

TABLE 2

XRPD peaks of Example 2

| Peak | Angle (°2-Theta) +/−0.2° | Relative Intensity (% of most intense peak) |
|---|---|---|
| 1 | 5.7 | 31.9 |
| 2 | 6.5 | 85.7 |
| 3 | 9.8 | 90.7 |
| 4 | 13.0 | 56.9 |
| 5 | 13.5 | 26.8 |
| 6 | 14.6 | 84.2 |
| 7 | 16.5 | 34.7 |
| 8 | 17.1 | 56.0 |
| 9 | 18.9 | 58.7 |
| 10 | 19.7 | 100 |
| 11 | 23.8 | 85.6 |
| 12 | 24.5 | 70.1 |

Example 3

4-[4-[3-Chloro-4-[2-hydroxy-1-(2-pyridyl)ethoxy]pyrazolo[1,5-a]pyridin-6-yl]-5-methyl-triazol-1-yl]piperidine-1-carbonitrile, Isomer 1, Mono-Gallic Acid Cocrystalline Form ("the Cocrystalline Form of Formula V")

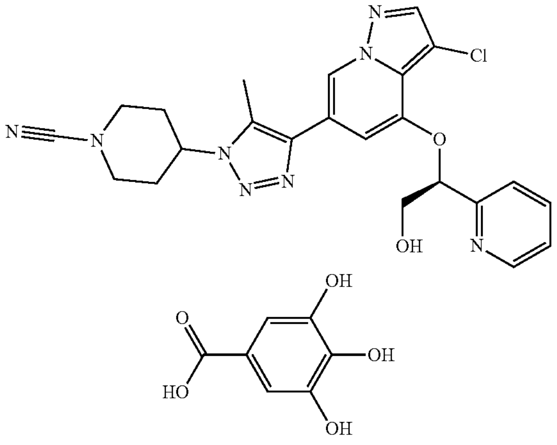

4-[4-[3-chloro-4-[2-hydroxy-1-(2-pyridyl)ethoxy]pyrazolo[1,5-a]pyridin-6-yl]-5-methyl-triazol-1-yl]piperidine-1-carbonitrile, Isomer 1 (9.76 g) is dissolved in ethyl acetate. Gallic acid (4.23 g) is added and the resulting slurry is filtered. The solids are taken up in ethyl acetate (60 mL) and stirred at 45° C. for 30 min. The resulting slurry is filtered. The solids are taken up in ethyl acetate (50 mL) and stirred at room temperature for 2 days. The resulting slurry is filtered. The solids are dried under a nitrogen stream for 15 min and in a vacuum oven (75° C. for 2 hours). The solids are taken up in cyclopentyl methyl ether (40 mL) and stirred at room temperature for 5 days. The resulting slurry is filtered and dried at 75° C. overnight. The solids are taken up in cyclopentyl methyl ether (40 mL) and stirred at room temperature for 1 day. The resulting slurry is filtered and dried at 75° C. overnight to give the title compound (8.9 g).

XRPD of 4-[4-[3-chloro-4-[2-hydroxy-1-(2-pyridyl)ethoxy]pyrazolo[1,5-a]pyridin-6-yl]-5-methyl-triazol-1-yl]piperidine-1-carbonitrile, Isomer 1, Mono-Gallic Acid Cocrystalline Form ("the Cocrystalline Form of Formula V")

A prepared sample of the cocrystalline form of Formula V is characterized by an XRPD pattern using CuKα radiation as having diffraction peaks (2-theta values) as described in Table 3, and in particular having a peak at 6.9 in combination with one or more of the peaks selected from the group consisting of 12.7, 18.4, 9.1, and 23.4; with a tolerance for the diffraction angles of ±0.2 degrees.

TABLE 3

XRPD peaks of Example 3

| Peak | Angle (°2-Theta) +/−0.2° | Relative Intensity (% of most intense peak) |
|---|---|---|
| 1 | 6.9 | 100 |
| 2 | 9.1 | 27.7 |
| 3 | 10.5 | 17.1 |
| 4 | 12.7 | 59.5 |
| 5 | 15.7 | 18.2 |
| 6 | 16.3 | 26.6 |
| 7 | 16.8 | 21.5 |
| 8 | 17.1 | 13.6 |
| 9 | 17.9 | 21.0 |
| 10 | 18.4 | 84.8 |
| 11 | 21.0 | 17.4 |
| 12 | 23.4 | 31.9 |

Example 4

4-[4-[3-Chloro-4-[2-hydroxy-1-(2-pyridyl)ethoxy]pyrazolo[1,5-a]pyridine-6-yl]-5-methyl-triazol-1-yl]piperidine-1-carbonitrile, Isomer 1, Mono-Nicotinamide Cocrystalline Form ("the Cocrystalline Form of Formula VI")

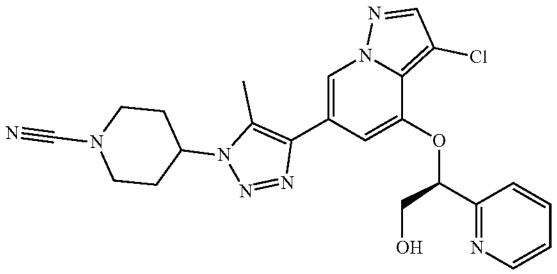

-continued

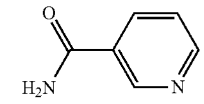

4-[4-[3-chloro-4-[2-hydroxy-1-(2-pyridyl)ethoxy]pyrazolo[1,5-a]pyridine-6-yl]-5-methyl-triazol-1-yl]piperidine-1-carbonitrile, Isomer 1 (0.253 g)

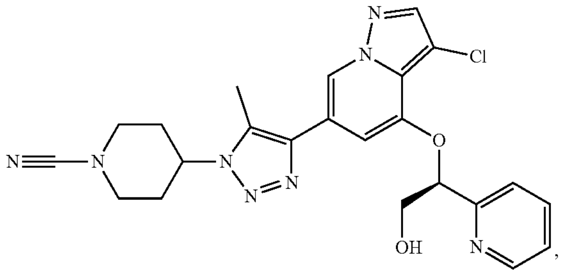 [SMILES: Cc1c(-c2cc(O[C@H](CO)c3ccccn3)c3c(Cl)cnn3c2)nnn1C1CCN(C#N)CC1]

is dissolved in ethyl acetate (8 mL, saturated with nicotinamide) and stirred at room temperature for 35 min. The resulting slurry is filtered. The solids are dried in place under vacuum and under a nitrogen stream for 15 min to give the title compound (0.236 g).

XRPD of 4-[4-[3-Chloro-4-[2-hydroxy-1-(2-pyridyl)ethoxy]pyrazolo[1,5-a]pyridine-6-yl]-5-methyl-triazol-1-yl]piperidine-1-carbonitrile, Isomer 1, Mono-Nicotinamide Cocrystalline Form ("the Cocrystalline Form of Formula VI")

A prepared sample of the cocrystalline form of Formula VI is characterized by an XRPD pattern using CuKα radiation as having diffraction peaks (2-theta values) as described in Table 4, and in particular having a peak at 13.7 in combination with one or more of the peaks selected from the group consisting of 9.6, 17.9, and 24.7; with a tolerance for the diffraction angles of ±0.2 degrees.

TABLE 4

XRPD peaks of Example 4

| Peak | Angle (°2-Theta) +/−0.2° | Relative Intensity (% of most intense peak) |
|---|---|---|
| 1 | 6.8 | 13.4 |
| 2 | 8.2 | 42.5 |
| 3 | 9.6 | 66.1 |
| 4 | 12.3 | 20.8 |
| 5 | 13.7 | 67.2 |
| 6 | 15.8 | 18.4 |
| 7 | 17.5 | 37.2 |
| 8 | 17.9 | 83.4 |
| 9 | 18.7 | 63.0 |
| 10 | 19.0 | 23.2 |
| 11 | 22.2 | 61.8 |
| 12 | 22.9 | 14.7 |
| 13 | 24.7 | 100 |
| 14 | 26.1 | 62.6 |

Example 5A

4-[4-[3-Chloro-4-[1-(5-fluoro-2-pyridyl)-2-hydroxy-ethoxy]pyrazolo[1,5-a]pyridin-6-yl]-5-methyl-tri-azol-1-yl]piperidine-1-carbonitrile, Isomer 2, 30% SDD (Spray Dried Dispersion) with IPMC ("Isomer 2 IPMC SDD")

4-[4-[3-Chloro-4-[1-(5-fluoro-2-pyridyl)-2-hydroxy-ethoxy]pyrazolo[1,5-a]pyridin-6-yl]-5-methyl-triazol-1-yl] piperidine-1-carbonitrile, Isomer 2 (300.66 mg) is dissolved in acetone (10 mL) and methanol (10 mL). IPMC (hydroxypropyl methylcellulose; 702.19 mg) is added and the materials are vortex mixed for 20-30 minutes. The material is spray dried (water bath 60° C., oil bath 200° C., nitrogen 60 psi, starting temperature 45° C., final temperature 72° C., 1 mL/min, 15-20 min) to give the title compound (615 mg, 61%).

Example 5B

4-[4-[3-Chloro-4-[1-(5-fluoro-2-pyridyl)-2-hydroxy-ethoxy]pyrazolo[1,5-a]pyridin-6-yl]-5-methyl-tri-azol-1-yl]piperidine-1-carbonitrile, Isomer 2, 30% SDD (Spray Dried Dispersion) with HPMC-AS-M ("Isomer 2 HPMC-AS-M SDD")

4-[4-[3-Chloro-4-[1-(5-fluoro-2-pyridyl)-2-hydroxy-ethoxy]pyrazolo[1,5-a]pyridin-6-yl]-5-methyl-triazol-1-yl] piperidine-1-carbonitrile, Isomer 2 (300.06 mg) is dissolved in acetone (10 mL) and methanol (10 mL). HPMC-AS-M (hydroxypropyl methylcellulose acetate succinate; 701.13 mg) is added and the materials are vortex mixed for 20 minutes. The material is spray dried (water bath 60° C., oil bath 200° C., nitrogen 60 psi, starting temperature 45° C., final temperature 72° C., 4 mL/min, 5-10 min) to give the title compound (781 mg, 78%).

Example 5C

4-[4-[3-Chloro-4-[1-(5-fluoro-2-pyridyl)-2-hydroxy-ethoxy]pyrazolo[1,5-a]pyridin-6-yl]-5-methyl-tri-azol-1-yl]piperidine-1-carbonitrile, Isomer 2, 30% SDD (Spray Dried Dispersion) with PVP-VA ("Isomer 2 PVP-VA SDD")

4-[4-[3-Chloro-4-[1-(5-fluoro-2-pyridyl)-2-hydroxy-ethoxy]pyrazolo[1,5-a]pyridin-6-yl]-5-methyl-triazol-1-yl] piperidine-1-carbonitrile, Isomer 2 (301.48 mg) is dissolved in acetone (10 mL) and methanol (10 mL). PVP-VA (poly (1-vinylpyrrolidone-co-vinyl acetate; 703.28 mg) is added and the materials are vortex mixed for 1 minute. The material is spray dried (water bath 60° C., oil bath 200° C., nitrogen 60 psi, starting temperature 45° C., final temperature 72° C., 2 mL/min, 10 min) to give the title compound (907 mg, 90%).

Approximate 2 mg/ml samples of Isomer 2 IPMC SDD, Isomer 2 HPMC-AS-M SDD, Isomer 2 PVP-VA SDD, and the cocrystalline form of Formula I or Formula II in Table 5 media were prepared. 2 mg/ml samples of Isomer 2 IPMC SDD, Isomer 2 HPMC-AS-M SDD, Isomer 2 PVP-VA SDD, and the cocrystalline form of Formula I or Formula II were placed in a rotating mixer or rotating stirrer for approximately 2 hours or approximately 24 hours. Samples of Isomer 2 IPMC SDD, Isomer 2 HPMC-AS-M SDD, Isomer 2 PVP-VA SDD, and the cocrystalline form of Formula I or Formula II were centrifuged. The sample supernatants of Isomer 2 IPMC SDD, Isomer 2 HPMC-AS-M SDD, Isomer 2 PVP-VA SDD, and the cocrystalline form of Formula I or Formula II were analyzed by HPLC using the following conditions: Agilent ZORBAX Bonus-RP, Rapid Resolution, 4.6*75, 3.5 um; eluting with a gradient of 95% to 5% to 95% H2O in ACN (0.1% TFA), flow rate: 1.5 mL/min.

TABLE 5

Solubility of Isomer 2 freebase, Isomer 2 HPMC SDD, and the cocrystalline form of Formula I or Formula II

| Media | Isomer 2 Free Base Solubility @ 24 hrs (mg/mL) | Isomer 2 HPMC SDD Solubility @ 24 hrs (mg/mL) | Cocrystalline form of Formula I or Formula II Solubility @ 24 hrs (mg/mL) |
|---|---|---|---|
| 0.1N Aqueous HCl | 0.012 | 0.028 | 0.016 |
| 0.01N Aqueous HCl | 0.007 | 0.014 | 0.009 |
| Simulated Gastric Fluid | 0.047 | 0.019 | 0.066 |
| Water | 0.006 | 0.012 | 0.008 |
| pH 4.5 (Acetate Buffer USP) | 0.006 | 0.014 | 0.007 |
| Simulated Intestinal Fluid (Fed) | 0.038 | 0.058 | 0.048 |
| Simulated Intestinal Fluid (Fasted) | 0.010 | 0.019 | 0.047 |
| pH 6.0 (Phosphate Buffer USP) | 0.006 | 0.012 | 0.006 |
| pH 7.5 (Phosphate Buffer USP) | 0.005 | 0.012 | 0.006 |

Example 6

Samples of Isomer 2 HPMC SDD, Isomer 2 HPMC-AS-M SDD, Isomer 2 PVP-VA SDD, and the cocrystalline form of Formula I or Formula II were placed in a 40° C./75% RH chamber with the caps off. Samples of Isomer 2 HPMC SDD, Isomer 2 HPMC-AS-M SDD, Isomer 2 PVP-VA SDD, and the cocrystalline form of Formula I or Formula II were removed from the chamber after either 7 or 14 days.

Isomer 2 HPMC SDD was observed as partially deliquesced at all 40° C./75% RH time points. Isomer 2 PVP-VA SDD was observed as completely deliquesced at all 40° C./75% RH time points. Isomer 2 HPMC-AS-M SDD was observed as fine, white powder at all 40° C./75% RH time points. The cocrystalline form of Formula I or Formula II was observed as flowable white powder at all 40° C./75% RH time points.

Samples were analyzed by HPLC using the following conditions: Agilent ZORBAX Bonus-RP, Rapid Resolution, 4.6*75, 3.5 um; eluting with a gradient of 95% to 5% to 95% H2O in ACN (0.1% TFA), flow rate: 1.5 mL/min.

TABLE 6

Solid state stability of Isomer 2 HPMC SDD, Isomer 2 HPMC-AS-M SDD, Isomer 2 PVP-VA SDD, and the cocrystalline form of Formula I or Formula II

| Form | 7 Days Percent Remaining | 14 Days Percent Remaining |
|---|---|---|
| Cocrystalline form of Formula I or Formula II | 84.97 | 84.59 |
| Isomer 2 HPMC SDD | 30.7 | 29.4 |
| Isomer 2 HPMC-AS-M SDD | 31.5 | 28.0 |
| Isomer 2 PVP-VA SDD | 29.7 | 29.1 |

Embodiment 1. A cocrystalline form of ("Isomer 2")

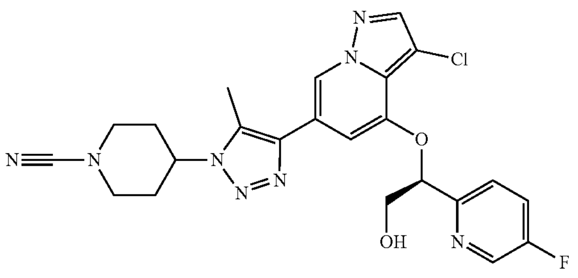

and a gallic acid coformer.

Embodiment 2. The cocrystalline form of embodiment 1 wherein the ratio of Isomer 2 to gallic acid is about 2:1.

Embodiment 3. The cocrystalline form of embodiments 1 or 2 wherein the water content ranges from about 0% to about 3.2%.

Embodiment 4. The cocrystalline form of any one of embodiments 1 to 3 wherein the cocrystalline form is Formula I:

(Formula I)

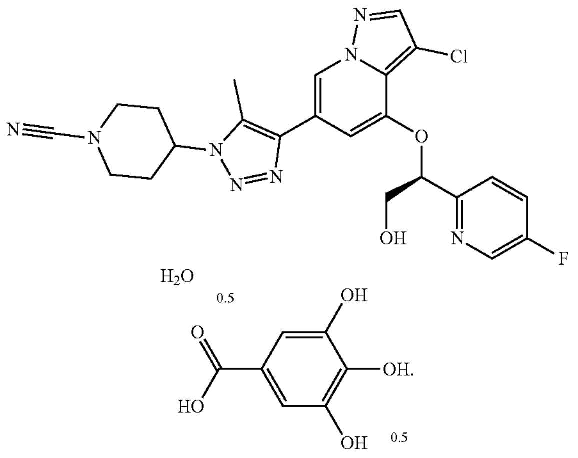

Embodiment 5. The cocrystalline form of embodiment 4 that is dehydrated or partially dehydrated.

Embodiment 6. The cocrystalline form of any one of embodiments 1 to 3 wherein the cocrystalline form is Formula II:

(Formula II)

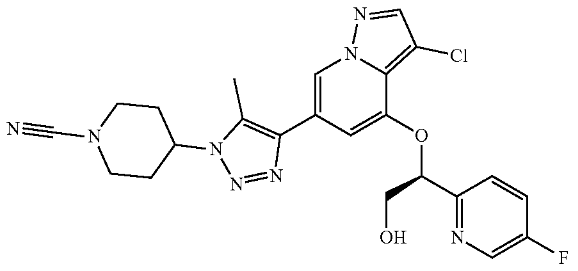

-continued

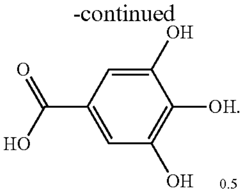

Embodiment 7. The cocrystalline form of any one of embodiments 1 to 6 characterized by having an XRPD pattern using CuKα radiation comprising a peak at 8.4° and one or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees.

Embodiment 8. The cocrystalline form of any one of embodiments 1 to 7 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4°; with a tolerance for the diffraction angles of ±0.2 degrees.

Embodiment 9. The cocrystalline form of any one of embodiments 1 to 8 characterized by an XRPD pattern using CuKα radiation having a diffraction peak at diffraction angle 2-theta of 8.4° in combination with two or more of the peaks selected from the group consisting of 15.6°, 21.3°, 6.7°, and 23.4°; with a tolerance for the diffraction angles of ±0.2 degrees.

Embodiment 10. The cocrystalline form of any one of embodiments 1 to 9 characterized by an XRPD pattern using CuKα radiation having a diffraction peak at diffraction angle 2-theta of 8.4° in combination with three or more of the peaks selected from the group consisting of 15.6°, 21.3°, 6.7°, and 23.4°; with a tolerance for the diffraction angles of ±0.2 degrees.

Embodiment 11. The cocrystalline form of any one of embodiments 1 to 8 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4° and in combination with one or more of the peaks selected from the group consisting of 9.2°, 10.0°, 13.4°, 14.1°, 16.9°, 18.4°, 19.6°, and 24.2° with a tolerance for the diffraction angles of ±0.2 degrees.

Embodiment 12. The cocrystalline form of any one of embodiments 1 to 11 characterized by a $^{13}C$ solid state NMR spectrum which comprises peaks referenced to the carbonyl resonance of glycine selected from the group consisting of 8.1, 11.1, 26.6, 28.2, 32.3, 35.0, 80.7, 81.7, 99.6, 102.3, 110.9, 158.0, 160.0, 168.2, and 175.0, with a tolerance of ±0.2 ppm.

Embodiment 13. A cocrystalline form of Formula I, (Formula I)

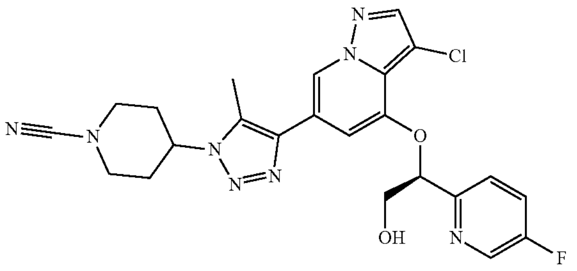

-continued

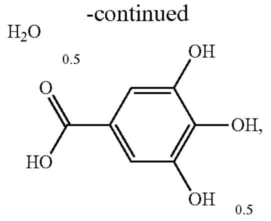

obtainable by adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 and gallic acid to a solvent to give a slurry, and adding cyclopentyl methyl ether to the slurry to form a white precipitate.

Embodiment 14. The cocrystalline form of embodiment 13, wherein the solvent comprises THF.

Embodiment 15. The cocrystalline form of embodiments 13 or 14, wherein the slurry is seeded with the cocrystalline form of Formula I.

Embodiment 16. A cocrystalline form of Formula II:

(Formula II)

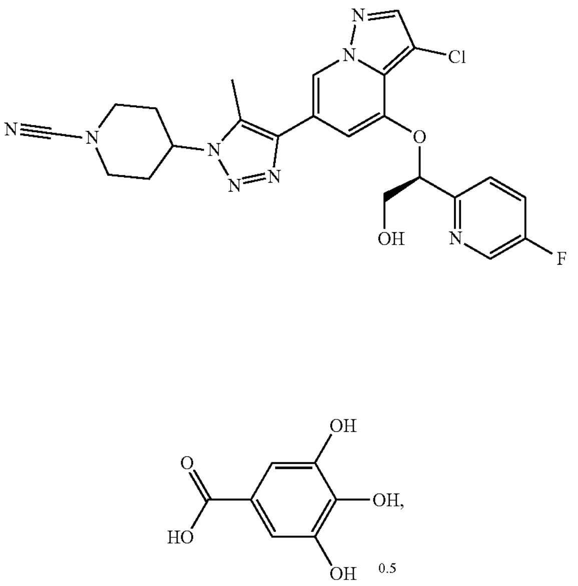

obtainable by heating a cocrystalline form of Formula I:

(Formula I)

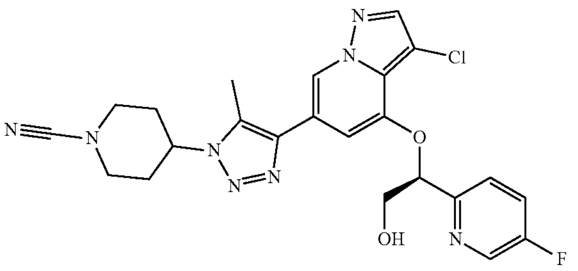

-continued

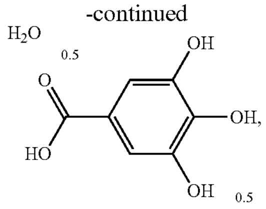

to form a dehydrated hydrate.

Embodiment 17. The cocrystalline form of embodiment 16 wherein the step of heating is from approximately 25° C. to 200° C. at a rate of 10° C./min.

Embodiment 18. The cocrystalline form of embodiments 16 or 17 wherein nitrogen is the carrier gas at about 10 mL/min.

Embodiment 19. The cocrystalline form of any one of embodiments 16 to 18 wherein nitrogen is the purge gas at about 50 mL/min.

Embodiment 20. The cocrystalline form of embodiment 1 wherein the ratio of Isomer 2 to gallic acid is about 1:1.

Embodiment 21. The cocrystalline form of embodiments 1 or 20 wherein the cocrystalline form is

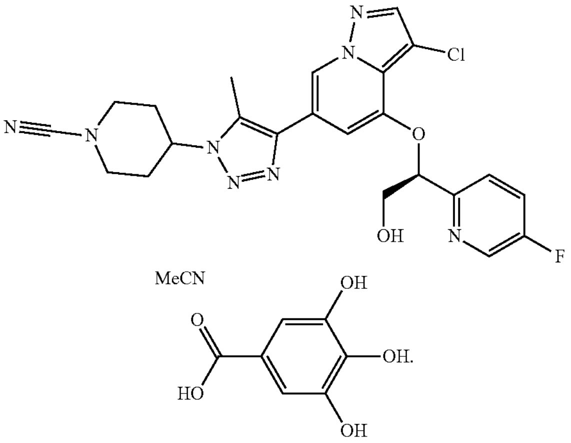

Embodiment 22. The cocrystalline form of any one of embodiments 1, 20, or 21 characterized by having an XRPD pattern using CuKα radiation comprising a peak at 14.6° and one or more peaks at 5.7°, 6.5°, 9.8°, 13.0°, 13.5°, 16.5°, 17.10, 18.9°, 19.7°, 23.8°, or 24.5° with a tolerance for the diffraction angles of ±0.2 degrees.

Embodiment 23. The cocrystalline form of any one of embodiments 1, or 20-22 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7°; with a tolerance for the diffraction angles of ±0.2 degrees.

Embodiment 24. The cocrystalline form of any one of embodiments 1, or 20-23 characterized by an XRPD pattern using CuKα radiation having a diffraction peak at diffraction angle 2-theta of 14.6° in combination with two or more of the peaks selected from the group consisting of 9.8°, 23.8°, 6.5°, and 19.7°; with a tolerance for the diffraction angles of ±0.2 degrees.

Embodiment 25. The cocrystalline form of any one of embodiments 1, or 20-24 characterized by an XRPD pattern using CuKα radiation having a diffraction peak at diffraction angle 2-theta of 14.6° in combination with three or more of the peaks selected from the group consisting of 9.8°, 23.8°, 6.5°, and 19.7°; with a tolerance for the diffraction angles of ±0.2 degrees.

Embodiment 26. The cocrystalline form of any one of embodiments 1, 20-25 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7° and in combination with one or more of the peaks selected from the group consisting of 5.7°, 13.0°, 13.5°, 16.5°, 17.1°, 18.9°, and 24.5° with a tolerance for the diffraction angles of ±0.2 degrees.

Embodiment 27. A cocrystalline form,

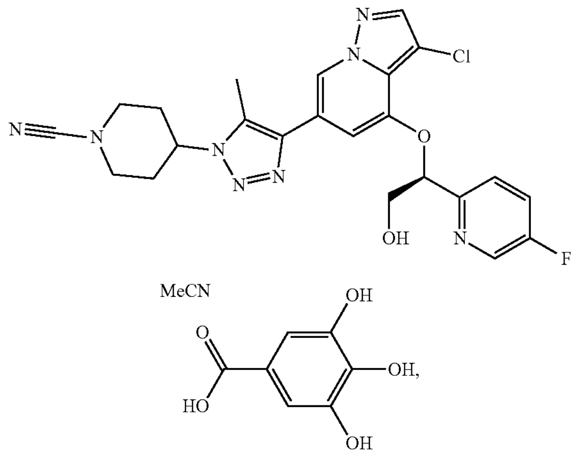

obtainable by combining

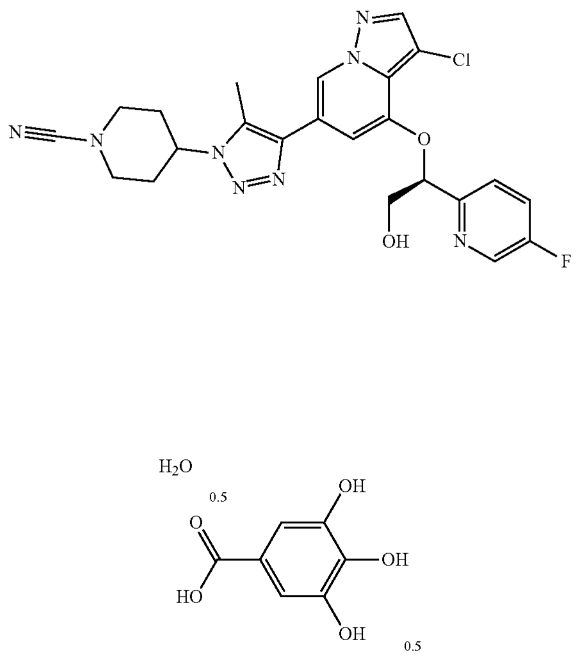

with acetonitrile.

Embodiment 28. A cocrystalline form of

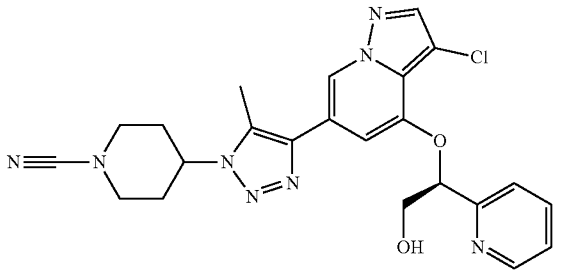 [SMILES: Cc1c(-c2cc(O[C@H](CO)c3ccccn3)c3c(Cl)cnn3c2)nnn1C1CCN(C#N)CC1]

and a gallic acid coformer.

Embodiment 29. The cocrystalline form of embodiment 28 wherein the ratio of Isomer A to gallic acid is about 1:1.

Embodiment 30. The cocrystalline form of embodiments 28 or 29 wherein the cocrystalline form is

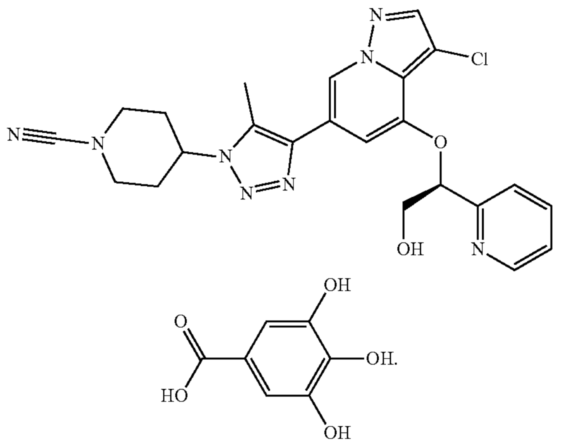 [SMILES: Cc1c(-c2cc(O[C@H](CO)c3ccccn3)c3c(Cl)cnn3c2)nnn1C1CCN(C#N)CC1 ; O=C(O)c1cc(O)c(O)c(O)c1]

Embodiment 31. The cocrystalline form of any one of embodiments 28 to 30 characterized by having an XRPD pattern using CuKα radiation comprising a peak at 6.9° and one or more peaks at 9.10, 10.5°, 12.7°, 15.7°, 16.3°, 16.8°, 17.10, 17.9°, 18.4°, 21.0°, or 23.4° with a tolerance for the diffraction angles of ±0.2 degrees.

Embodiment 32. The cocrystalline form of any one of embodiments 28 to 31 characterized by having an XRPD pattern using CuKα radiation comprising a peak at 6.9° in combination with one or more of the peaks selected from the group consisting of 12.7°, 18.4°, 9.10, and 23.4° with a tolerance for the diffraction angles of ±0.2 degrees.

Embodiment 33. The cocrystalline form of any one of embodiments 28 to 32 characterized by having an XRPD pattern using CuKα radiation comprising a peak at 6.9° in combination with two or more of the peaks selected from the group consisting of 12.7°, 18.4°, 9.10, and 23.4° with a tolerance for the diffraction angles of ±0.2 degrees.

Embodiment 34. The cocrystalline form of any one of embodiments 28 to 33 characterized by having an XRPD pattern using CuKα radiation comprising a peak at 6.9° in combination with three or more of the peaks selected from the group consisting of 12.7°, 18.4°, 9.10, and 23.4° with a tolerance for the diffraction angles of ±0.2 degrees.

Embodiment 35. The cocrystalline form of any one of embodiments 28 to 31 characterized by having an XRPD pattern using CuKα radiation comprising a peak at 6.9° in combination with one or more of the peaks selected from the group consisting of 12.7°, 18.4°, 9.10, and 23.4° and in combination with one or more of the peaks selected from the group consisting of 9.10, 10.5°, 12.7°, 15.7°, 16.3°, 16.8°, 17.1°, 17.9°, 18.4°, 21.0°, and 23.4° with a tolerance for the diffraction angles of ±0.2 degrees.

Embodiment 36. A cocrystalline form,

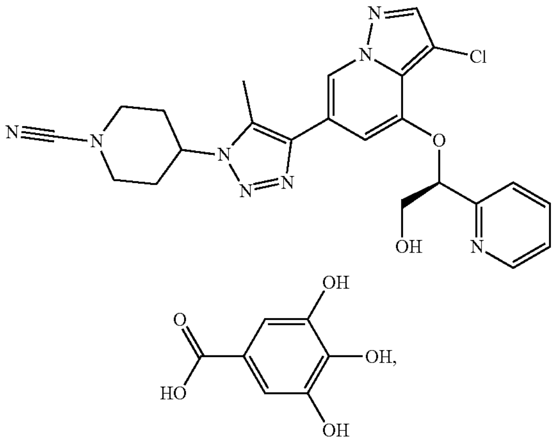 [SMILES: Cc1c(-c2cc(O[C@H](CO)c3ccccn3)c3c(Cl)cnn3c2)nnn1C1CCN(C#N)CC1 ; O=C(O)c1cc(O)c(O)c(O)c1]

obtainable by adding gallic acid to

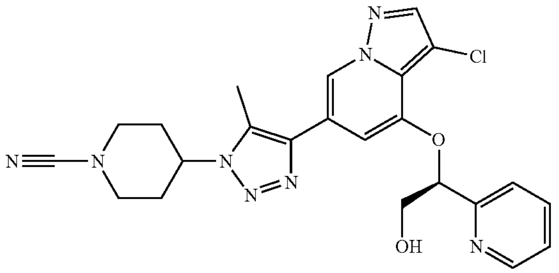 [SMILES: Cc1c(-c2cc(O[C@H](CO)c3ccccn3)c3c(Cl)cnn3c2)nnn1C1CCN(C#N)CC1]

dissolved in ethyl acetate.

Embodiment 37. A pharmaceutical composition comprising the cocrystalline form according to any one of embodiments 1 to 36 and further comprising a pharmaceutically acceptable carrier, diluent or excipient.

Embodiment 38. The pharmaceutical composition of embodiment 37, wherein the composition contains at least about 80% by wt. of any of the cocrystalline forms.

Embodiment 39. The pharmaceutical composition of embodiment 37 or 38, wherein the composition contains at least about 90% by wt. of any of the cocrystalline forms.

Embodiment 40. The pharmaceutical composition of any one of embodiments 37 to 39 wherein the composition contains at least about 95% by wt. of any of the cocrystalline forms.

Embodiment 41. A method of treating cancer comprising administering to a patient in need thereof an effective amount of the cocrystalline forms according to any one of embodiments 1 to 36.

Embodiment 42. A method of treating cancer comprising administering to a patient in need thereof an effective amount of the pharmaceutical compositions according to any one of embodiments 37 to 40.

Embodiment 43. The method of embodiments 41 or 42, wherein the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 44. The method of any one of embodiments 41 to 43, wherein the cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

Embodiment 45. The method of any one of embodiments 41 to 44, wherein the cancer is urothelial cancer.

Embodiment 46. The method of any one of embodiments 41 to 44, wherein the cancer is bladder cancer.

Embodiment 47. The method of any one of embodiments 41 to 44, wherein the cancer is urothelial bladder cancer.

Embodiment 48. The method of any one of embodiments 41 to 44, wherein the cancer is advanced urothelial bladder cancer.

Embodiment 49. The method of any one of embodiments 41 to 44, wherein the cancer is metastatic urothelial bladder cancer.

Embodiment 50. The method of any one of embodiments 41 to 44, wherein the cancer is non-muscle invasive bladder cancer.

Embodiment 51. The method of any one of embodiments 41 to 44, wherein the cancer is muscle invasive bladder cancer.

Embodiment 52. A method of inhibiting bladder cancer comprising administering to a patient in need thereof an effective amount of the cocrystalline form according to any one of embodiments 1 to 36.

Embodiment 53. A method of inhibiting bladder cancer comprising administering to a patient in need thereof an effective amount of the pharmaceutical composition according to any one of embodiments 37 to 40.

Embodiment 54. The cocrystalline form according to any one of embodiments 1 to 36 for use in therapy.

Embodiment 55. The cocrystalline form according to any one of embodiments 1 to 36 for use in treatment of cancer.

Embodiment 56. The cocrystalline form for use according to embodiments 54 or 55, wherein the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 57. The cocrystalline form for use according to embodiments 55 or 56, wherein the cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

Embodiment 58. The cocrystalline form for use according to any one of embodiments 55 to 57, wherein the cancer is urothelial cancer.

Embodiment 59. The cocrystalline form for use according to any one of embodiments 55 to 57, wherein the cancer is bladder cancer.

Embodiment 60. The cocrystalline form for use according to any one of embodiments 55 to 57, wherein the cancer is urothelial bladder cancer.

Embodiment 61. The cocrystalline form for use according to any one of embodiments 55 to 57, wherein the cancer is advanced urothelial bladder cancer.

Embodiment 62. The cocrystalline form for use according to any one of embodiments 55 to 57, wherein the cancer is metastatic urothelial bladder cancer.

Embodiment 63. The cocrystalline form for use according to any one of embodiments 55 to 57, wherein the cancer is non-muscle invasive bladder cancer.

Embodiment 64. The cocrystalline form for use according to any one of embodiments 55 to 57, wherein the cancer is muscle invasive bladder cancer.

Embodiment 65. The pharmaceutical composition according to any one of embodiments 37 to 40 for use in therapy.

Embodiment 66. The pharmaceutical composition according to any one of embodiments 37 to 40 for use in treatment of cancer.

Embodiment 67. The pharmaceutical composition for use according to embodiment 66, wherein the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 68. The pharmaceutical composition for use according to embodiments 66 or 67, wherein the cancer is selected from the group consisting of urothelial cancer, bladder cancer, advanced urothelial cancer, metastatic urothelial cancer, non-muscle invasive urothelial cancer, and muscle invasive urothelial cancer.

Embodiment 69. The pharmaceutical composition for use according to embodiments 66 or 67, wherein the cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

Embodiment 70. The pharmaceutical composition for use according to any one of embodiments 66 to 67, wherein the cancer is urothelial cancer.

Embodiment 71. The pharmaceutical composition for use according to any one of embodiments 66 to 67, wherein the cancer is bladder cancer.

Embodiment 72. The pharmaceutical composition for use according to any one of embodiments 66 to 67, wherein the cancer is urothelial bladder cancer.

Embodiment 73. The pharmaceutical composition for use according to any one of embodiments 66 to 67, wherein the cancer is advanced urothelial bladder cancer.

Embodiment 74. The pharmaceutical composition for use according to any one of embodiments 66 to 67, wherein the cancer is metastatic urothelial bladder cancer.

Embodiment 75. The pharmaceutical composition for use according to any one of embodiments 66 to 67, wherein the cancer is non-muscle invasive bladder cancer.

Embodiment 76. The pharmaceutical composition for use according to any one of embodiments 66 to 67, wherein the cancer is muscle invasive bladder cancer.

Embodiment 77. Use of the cocrystalline forms according to any one of embodiments 1 to 36 in the manufacture of a medicament for treatment of cancer.

Embodiment 78. Use of the pharmaceutical composition according to any one of embodiments 37 to 40 in the manufacture of a medicament for treatment of cancer.

Embodiment 79. The use of embodiments 77 or 78, wherein the cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 80. The use of any one of embodiments 77 to 79, wherein the cancer is selected from the group consisting of urothelial cancer, bladder cancer, urothelial bladder cancer, advanced urothelial bladder cancer, metastatic urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, and muscle invasive bladder cancer.

Embodiment 81. The use of any one of embodiments 77 to 80, wherein the cancer is urothelial cancer.

Embodiment 82. The use of any one of embodiments 77 to 80, wherein the cancer is bladder cancer.

Embodiment 83. The use of any one of embodiments 77 to 80, wherein the cancer is urothelial bladder cancer.

Embodiment 84. The use of any one of embodiments 77 to 80, wherein the cancer is advanced urothelial bladder cancer.

Embodiment 85. The use of any one of embodiments 77 to 80, wherein the cancer is metastatic urothelial bladder cancer.

Embodiment 86. The use of any one of embodiments 77 to 80, wherein the cancer is non-muscle invasive bladder cancer.

Embodiment 87. The use of any one of embodiments 77 to 80, wherein the cancer is muscle invasive bladder cancer.

Embodiment 88. A method for the preparation of the cocrystalline form according to any one of embodiments 1 to 12, comprising the steps of:

adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 and gallic acid to a solvent to give a slurry, and adding cyclopentyl methyl ether to the slurry to form a white precipitate.

Embodiment 89. The method of embodiment 88, wherein the solvent is THF.

Embodiment 90. The method of embodiments 88 or 89, wherein the slurry is seeded with the cocrystalline form of Formula I.

Embodiment 91. A method for the preparation of the cocrystalline form according to any one of embodiments 1 to 3 or 5 to 12, comprising the step of heating

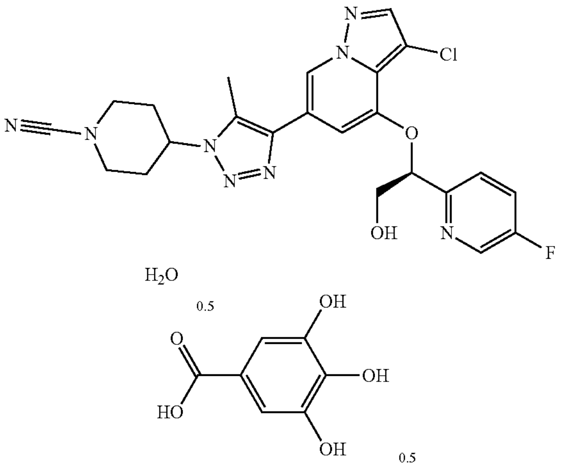

to form a dehydrated hydrate.

Embodiment 92. A method for the preparation of the cocrystalline form according to any one of embodiments 1 to 3, or 21 to 26, comprising the step of combining

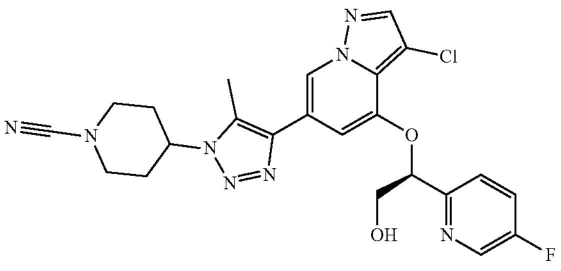

-continued

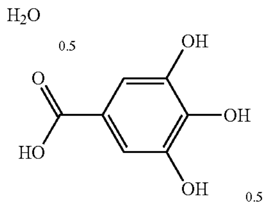

with acetonitrile.

Embodiment 93. A method for the preparation of the cocrystalline form according to any one of embodiments 28 to 35, comprising the step of adding gallic acid

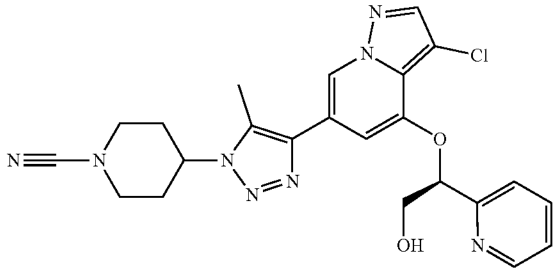 [SMILES: Cc1c(-c2cc(O[C@H](CO)c3ccccn3)c3c(Cl)cnn3c2)nnn1C1CCN(C#N)CC1]

dissolved in ethyl acetate.

Embodiment 94. A cocrystalline form of

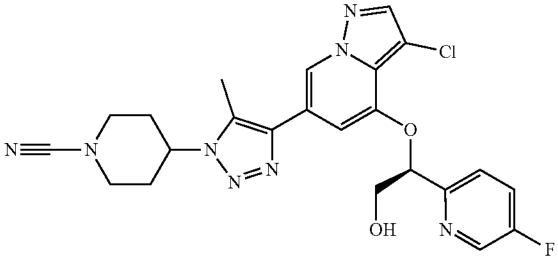 [SMILES: Cc1c(-c2cc(O[C@H](CO)c3ccc(F)cn3)c3c(Cl)cnn3c2)nnn1C1CCN(C#N)CC1]

("Isomer 2") and a gallic acid coformer.

Embodiment 95. The cocrystalline form of embodiment 94 wherein the ratio of Isomer 2 to gallic acid is about 2:1.

Embodiment 96. The cocrystalline form of embodiments 94 or 95 wherein water content ranges from about 0% to about 3.2%.

Embodiment 97. The cocrystalline form of any one of embodiments 94 to 96 wherein the cocrystalline form is

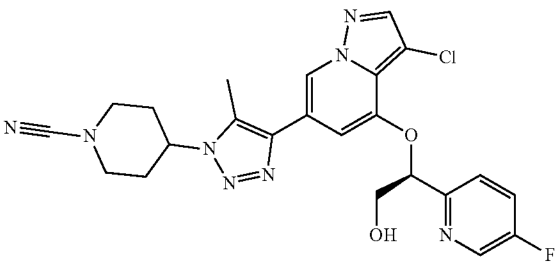

-continued

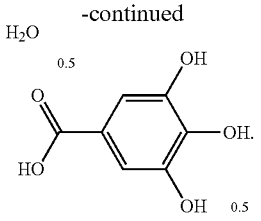

Embodiment 98. The cocrystalline form of embodiment 97 that is dehydrated or partially dehydrated.

Embodiment 99. The cocrystalline form of any one of embodiments 94 to 96, or 98 wherein the cocrystalline form is

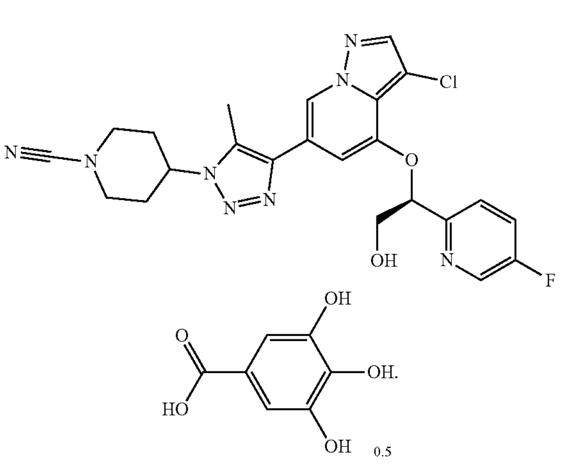

Embodiment 100. The cocrystalline form of any one of embodiments 94 to 99 characterized by having an XRPD pattern using CuKα radiation comprising a peak at 8.4° and one or more peaks at 6.7°, 9.2°, 10.0°, 13.4°, 14.10, 15.6°, 16.9°, 18.4°, 19.6°, 21.3°, 23.4°, or 24.2° with a tolerance for the diffraction angles of ±0.2 degrees.

Embodiment 101. The cocrystalline form of any one of embodiments 94 to 100 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4°; with a tolerance for the diffraction angles of ±0.2 degrees.

Embodiment 102. The cocrystalline form of any one of embodiments 94 to 101 characterized by an XRPD pattern using CuKα radiation having a diffraction peak at diffraction angle 2-theta of 8.4° in combination with two or more of the peaks selected from the group consisting of 15.6°, 21.3°, 6.7°, and 23.4°; with a tolerance for the diffraction angles of ±0.2 degrees.

Embodiment 103. The cocrystalline form of any one of embodiments 94 to 102 characterized by an XRPD pattern using CuKα radiation having a diffraction peak at diffraction angle 2-theta of 8.4° in combination with three or more of the peaks selected from the group consisting of 15.6°, 21.3°, 6.7°, and 23.4°; with a tolerance for the diffraction angles of ±0.2 degrees.

Embodiment 104. The cocrystalline form of any one of embodiments 94 to 103 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4° and in combination with one or more of the peaks selected from the group consisting of 9.2°, 10.0°, 13.4°, 14.10, 16.9°, 18.4°, 19.6°, and 24.2° with a tolerance for the diffraction angles of ±0.2 degrees.

Embodiment 105. The cocrystalline form of any one of embodiments 94 to 104 characterized by a $^{13}C$ solid state NMR spectrum which comprises peaks referenced to the carbonyl resonance of glycine selected from the group consisting of 8.1, 11.1, 26.6, 28.2, 32.3, 35.0, 80.7, 81.7, 99.6, 102.3, 110.9, 158.0, 160.0, 168.2, and 175.0, with a tolerance of ±0.2 ppm.

Embodiment 106. A cocrystalline form,

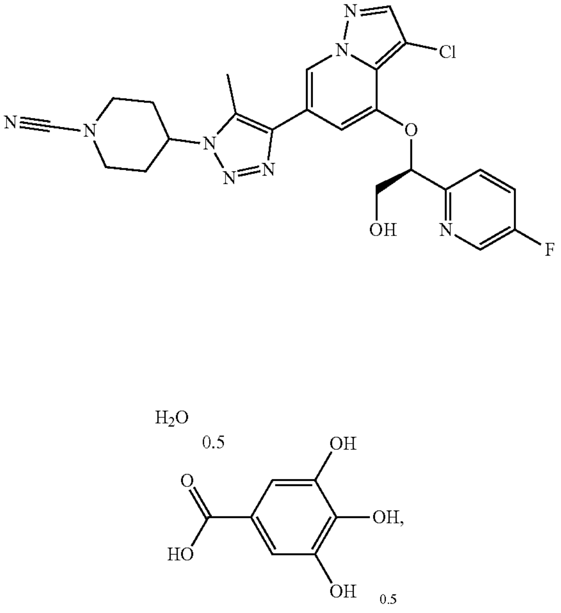

obtainable by adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 and gallic acid to a solvent to give a slurry, and adding cyclopentyl methyl ether to the slurry to form a white precipitate, wherein the crystalline form has improved solubility relative to a freebase form of Isomer 2:

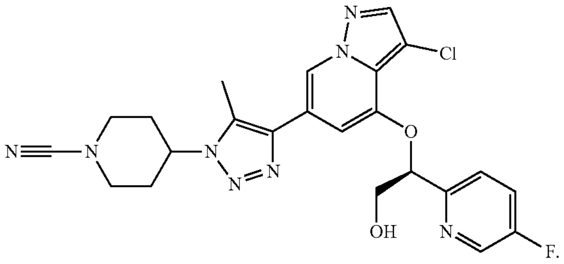 [SMILES: Cc1c(-c2cc(O[C@H](CO)c3ccc(F)cn3)c3c(Cl)cnn3c2)nnn1C1CCN(C#N)CC1]

Embodiment 107. The cocrystalline form of embodiment 106, wherein the solvent comprises THF.

Embodiment 108. The cocrystalline form of embodiments 106 or 107, wherein the slurry is seeded with the cocrystalline form.

Embodiment 109. A cocrystalline form,

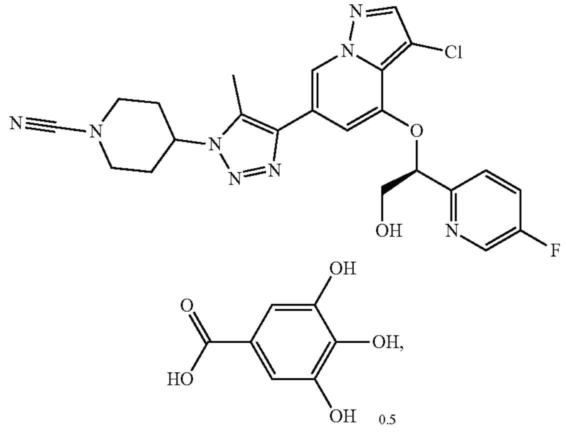

obtainable by heating

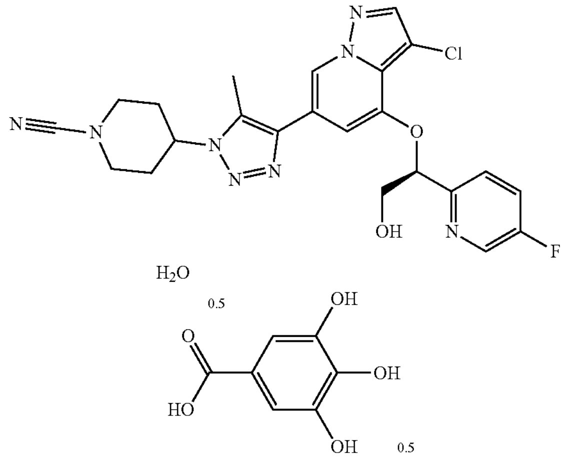

to form a dehydrated hydrate wherein the crystalline form has improved solubility relative to a freebase form of Isomer 2:

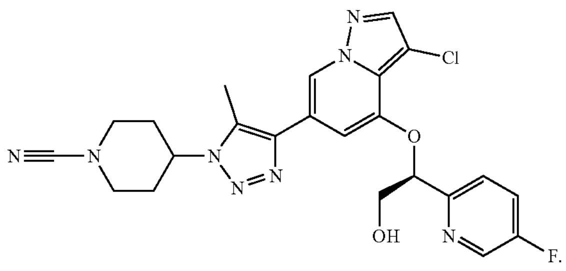 [SMILES: Cc1c(-c2cc(O[C@H](CO)c3ccc(F)cn3)c3c(Cl)cnn3c2)nnn1C1CCN(C#N)CC1]

Embodiment 110. The cocrystalline form of embodiment 109 wherein the step of heating is from approximately 25° C. to 200° C. at a rate of 10° C./min.

Embodiment 111. The cocrystalline form of embodiments 109 or 110 wherein nitrogen is a carrier gas at about 10 mL/min.

Embodiment 112. The cocrystalline form of any one of embodiments 109 to 111 wherein nitrogen is a purge gas at about 50 mL/min.

Embodiment 113. The cocrystalline form of embodiment 94 wherein the ratio of Isomer 2 to gallic acid is about 1:1.

Embodiment 114. The cocrystalline form of embodiments 94 or 113 wherein the cocrystalline form is

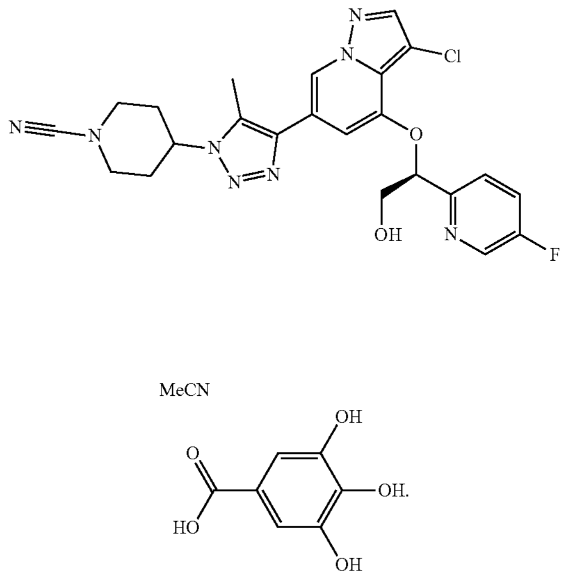

Embodiment 115. The cocrystalline form of any one of embodiments 94, 113, or 114 characterized by having an XRPD pattern using CuKα radiation comprising a peak at 14.6° and one or more peaks at 5.7°, 6.5°, 9.8°, 13.0°, 13.5°, 16.5°, 17.10, 18.9°, 19.7°, 23.8°, or 24.5° with a tolerance for the diffraction angles of ±0.2 degrees.

Embodiment 116. The cocrystalline form of any one of embodiments 94, or 113-115 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7°; with a tolerance for the diffraction angles of ±0.2 degrees.

Embodiment 117. The cocrystalline form of any one of embodiments 94, or 113-116 characterized by an XRPD pattern using CuKα radiation having a diffraction peak at diffraction angle 2-theta of 14.6° in combination with two or more of the peaks selected from the group consisting of 9.8°, 23.8°, 6.5°, and 19.7°; with a tolerance for the diffraction angles of ±0.2 degrees.

Embodiment 118. The cocrystalline form of any one of embodiments 94, or 113-116 characterized by an XRPD pattern using CuKα radiation having a diffraction peak at diffraction angle 2-theta of 14.6° in combination with three or more of the peaks selected from the group consisting of 9.8°, 23.8°, 6.5°, and 19.7°; with a tolerance for the diffraction angles of ±0.2 degrees.

Embodiment 119. The cocrystalline form of any one of embodiments 94, or 113-116 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7° and in combination with one or more of the peaks selected from the group consisting of 5.7°, 13.0°, 13.5°, 16.5°, 17.1°, 18.9°, and 24.5° with a tolerance for the diffraction angles of ±0.2 degrees.

Embodiment 120. A cocrystalline form,

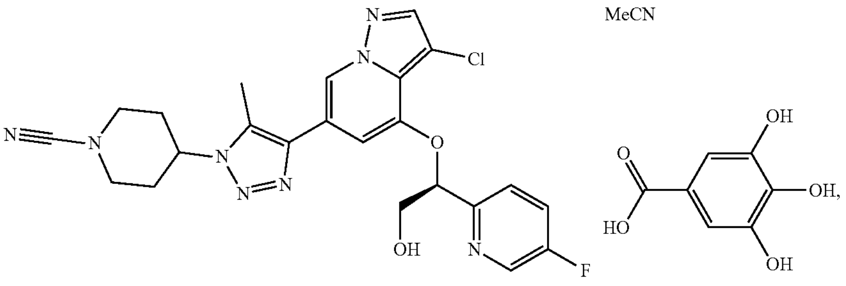

obtainable by combining

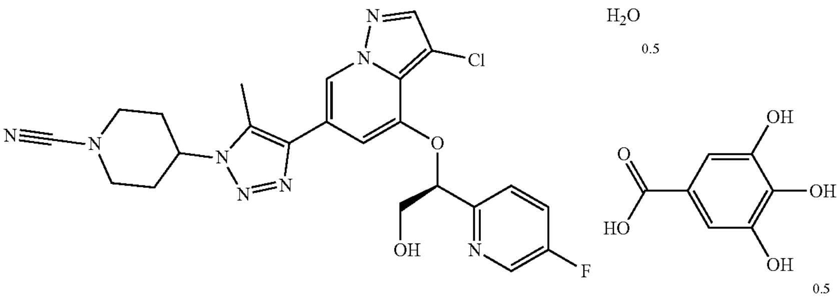

with acetonitrile, wherein the crystalline form has improved solubility relative to a freebase form of Isomer 2:

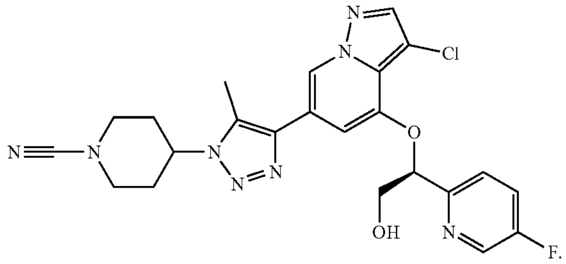 [SMILES: Cc1c(-c2cc(O[C@H](CO)c3ccc(F)cn3)c3c(Cl)cnn3c2)nnn1C1CCN(C#N)CC1]

Embodiment 121. A cocrystalline form of Isomer A:

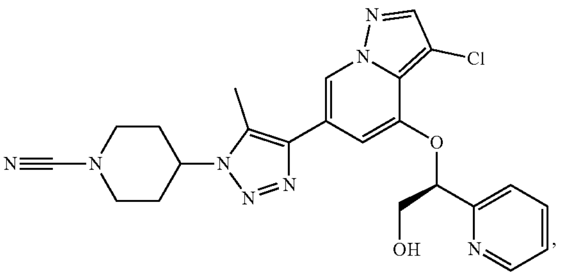 [SMILES: Cc1c(-c2cc(O[C@H](CO)c3ccccn3)c3c(Cl)cnn3c2)nnn1C1CCN(C#N)CC1]

and a gallic acid coformer or a nicotinamide coformer.

Embodiment 122. The cocrystalline form of embodiment 121 wherein the ratio of Isomer A to gallic acid is about 1:1.

Embodiment 123. The cocrystalline form of embodiments 121 or 122 wherein the cocrystalline form is

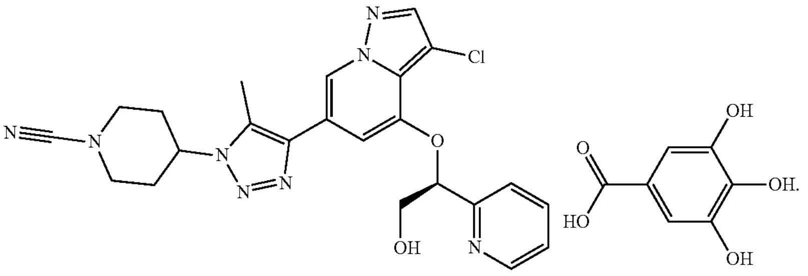

Embodiment 124. The cocrystalline form of any one of embodiments 121 to 123 characterized by having an XRPD pattern using CuKα radiation comprising a peak at 6.9° and one or more peaks at 9.1°, 10.5°, 12.7°, 15.7°, 16.3°, 16.8°, 17.10, 17.9°, 18.4°, 21.0°, or 23.4° with a tolerance for the diffraction angles of ±0.2 degrees.

Embodiment 125. The cocrystalline form of any one of embodiments 121 to 124 characterized by having an XRPD pattern using CuKα radiation comprising a peak at 6.9° in combination with one or more of the peaks selected from the group consisting of 12.7°, 18.4°, 9.10, and 23.4° with a tolerance for the diffraction angles of ±0.2 degrees.

Embodiment 126. The cocrystalline form of any one of embodiments 121 to 124 characterized by having an XRPD pattern using CuKα radiation comprising a peak at 6.9° in combination with two or more of the peaks selected from the group consisting of 12.7°, 18.4°, 9.10, and 23.4° with a tolerance for the diffraction angles of ±0.2 degrees.

Embodiment 127. The cocrystalline form of any one of embodiments 121 to 126 characterized by having an XRPD pattern using CuKα radiation comprising a peak at 6.9° in combination with three or more of the peaks selected from the group consisting of 12.7°, 18.4°, 9.10, and 23.4° with a tolerance for the diffraction angles of ±0.2 degrees.

Embodiment 128. The cocrystalline form of any one of embodiments 121 to 124 characterized by having an XRPD pattern using CuKα radiation comprising a peak at 6.9° in combination with one or more of the peaks selected from the group consisting of 12.7°, 18.4°, 9.10, and 23.4° and in combination with one or more of the peaks selected from the group consisting of 9.1°, 10.5°, 12.7°, 15.7°, 16.3°, 16.8°, 17.10, 17.9°, 18.4°, 21.0°, and 23.4° with a tolerance for the diffraction angles of ±0.2 degrees.

Embodiment 129. A cocrystalline form,

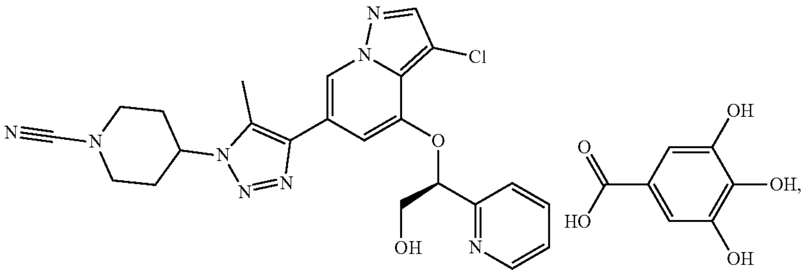

obtainable by adding gallic acid to

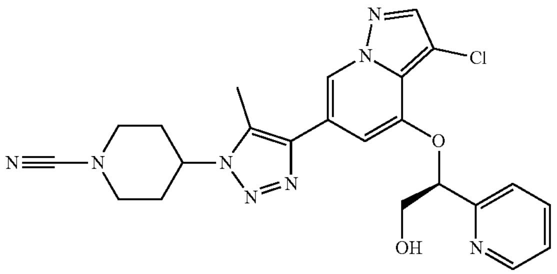 [SMILES: Cc1c(-c2cc(O[C@H](CO)c3ccccn3)c3c(Cl)cnn3c2)nnn1C1CCN(C#N)CC1]

dissolved in ethyl acetate, wherein the crystalline form has improved solubility relative to a freebase form of Isomer A:

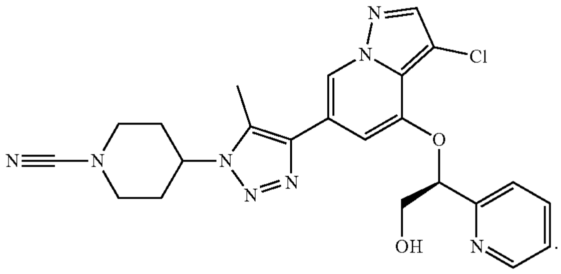 [SMILES: Cc1c(-c2cc(O[C@H](CO)c3ccccn3)c3c(Cl)cnn3c2)nnn1C1CCN(C#N)CC1].

Embodiment 130. The cocrystalline form of embodiment 121 wherein the ratio of Isomer A to nicotinamide is about 1:1.

Embodiment 131. The cocrystalline form of embodiments 121 or 130 wherein the cocrystalline form is

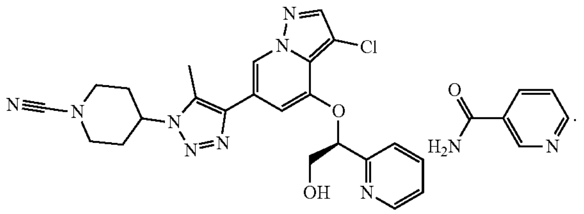.

Embodiment 132. The cocrystalline form of any one of embodiments 121, 130 to 131 characterized by having an XRPD pattern using CuKα radiation comprising a peak at 13.7° and one or more peaks at 6.8°, 8.2°, 9.6°, 12.3°, 15.8°, 17.5°, 17.9°, 18.7°, 19.0°, 22.2°, 22.9°, 24.7°, or 26.1° with a tolerance for the diffraction angles of ±0.2 degrees.

Embodiment 133. The cocrystalline form of any one of embodiments 121, 130 to 132 characterized by having an XRPD pattern using CuKα radiation comprising a peak at 13.7° in combination with one or more of the peaks selected from the group consisting of 9.6°, 17.9°, and 24.7° with a tolerance for the diffraction angles of ±0.2 degrees.

Embodiment 134. The cocrystalline form of any one of embodiments 121, 130 to 133 characterized by having an XRPD pattern using CuKα radiation comprising a peak at 13.7° in combination with two or more of the peaks selected from the group consisting of 9.6°, 17.9°, and 24.7° with a tolerance for the diffraction angles of ±0.2 degrees.

Embodiment 135. The cocrystalline form of any one of embodiments 121, 130 to 133 characterized by having an XRPD pattern using CuKα radiation comprising a peak at 13.7° in combination with the peaks selected from the group consisting of 9.6°, 17.9°, and 24.7° with a tolerance for the diffraction angles of ±0.2 degrees.

Embodiment 136. The cocrystalline form of any one of embodiments 121, 130 to 133 characterized by having an XRPD pattern using CuKα radiation comprising a peak at 13.7° in combination with one or more of the peaks selected from the group consisting of 9.6°, 17.9°, and 24.7° and in combination with one or more of the peaks selected from the group consisting of 6.8°, 8.2°, 12.3°, 15.8°, 17.5°, 18.7°, 19.0°, 22.2°, 22.9°, and 26.10 with a tolerance for the diffraction angles of ±0.2 degrees.

Embodiment 137. A cocrystalline form,

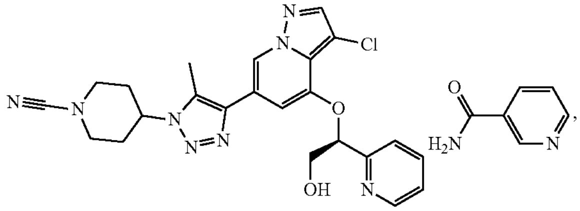, or a pharmaceutically acceptable salt thereof, obtainable by dissolving

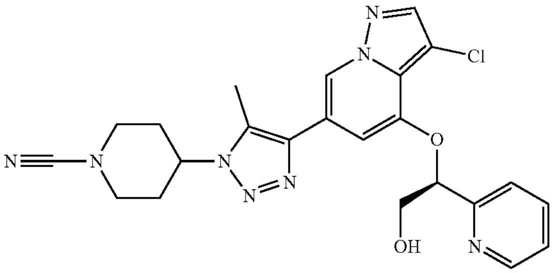 [SMILES: Cc1c(-c2cc(O[C@H](CO)c3ccccn3)c3c(Cl)cnn3c2)nnn1C1CCN(C#N)CC1]

in ethyl acetate saturated with nicotinamide, wherein the crystalline form has improved solubility relative to a freebase form of Isomer A:

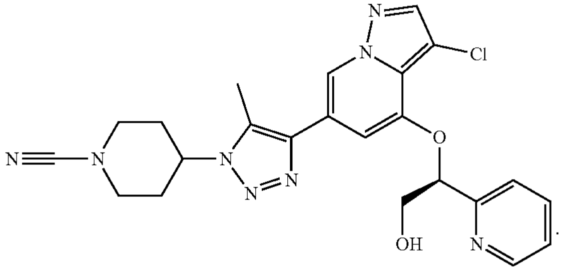 [SMILES: Cc1c(-c2cc(O[C@H](CO)c3ccccn3)c3c(Cl)cnn3c2)nnn1C1CCN(C#N)CC1].

Embodiment 138. A pharmaceutical composition comprising the cocrystalline form according to any one of embodiments 94 to 137 and further comprising a pharmaceutically acceptable carrier, diluent or excipient.

Embodiment 139. The pharmaceutical composition of embodiment 138, wherein the composition contains at least about 80% by wt. of the cocrystalline form.

Embodiment 140. The pharmaceutical composition of embodiments 138 or 139, wherein the composition contains at least about 90% by wt. of any of the cocrystalline forms.

Embodiment 141. The pharmaceutical composition of any one of embodiments 138 to 140 wherein the composition contains at least about 95% by wt. of any of the cocrystalline forms.

Embodiment 142. A method of treating a FGFR3-associated cancer comprising administering to a patient in need thereof an effective amount of a cocrystalline form according to any one of embodiments 94 to 137.

Embodiment 143. A method of treating a FGFR3-associated cancer comprising administering to a patient in need thereof an effective amount of the pharmaceutical compositions according to any one of embodiments 138 to 141.

Embodiment 144. The method of embodiments 142 or 143, wherein the FGFR3-associated cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 145. The method of any one of embodiments 142 to 144, wherein FGFR3-associated the cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

Embodiment 146. The method of any one of embodiments 142 to 144, wherein the FGFR3-associated cancer is urothelial cancer.

Embodiment 147. The method of any one of embodiments 142 to 144, wherein the FGFR3-associated cancer is intermediate risk non-muscle invasive bladder cancer.

Embodiment 148. The method of any one of embodiments 142 to 144, wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

Embodiment 149. The method of any one of embodiments 142 to 144, wherein the FGFR3-associated cancer is high risk non-muscle invasive bladder cancer.

Embodiment 150. The cocrystalline form according to any one of embodiments 94 to 137 for use in therapy.

Embodiment 151. The cocrystalline form according to any one of embodiments 94 to 137 for use in treatment of a FGFR3-associated cancer.

Embodiment 152. The cocrystalline form for use according to embodiment 151, wherein is the FGFR3-associated cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 153. The cocrystalline form for use according to embodiments 151 or 152, wherein is the FGFR3-associated cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

Embodiment 154. The cocrystalline form for use according to any one of embodiments 151 to 153, wherein the FGFR3-associated cancer is urothelial cancer.

Embodiment 155. The cocrystalline form for use according to any one of embodiments 151 to 153, wherein the FGFR3-associated cancer is bladder cancer.

Embodiment 156. The cocrystalline form for use according to any one of embodiments 151 to 153, wherein the FGFR3-associated cancer is urothelial bladder cancer.

Embodiment 157. The cocrystalline form for use according to any one of embodiments 151 to 153 wherein the FGFR3-associated cancer is advanced urothelial bladder cancer.

Embodiment 158. The cocrystalline form for use according to any one of embodiments 151 to 153, wherein the FGFR3-associated cancer is metastatic urothelial bladder cancer.

Embodiment 159. The cocrystalline form for use according to any one of embodiments 151 to 153, wherein the FGFR3-associated cancer is non-muscle invasive bladder cancer.

Embodiment 159. The cocrystalline form for use according to any one of embodiments 151 to 153, wherein the FGFR3-associated cancer is intermediate risk non-muscle invasive bladder cancer.

Embodiment 160. The cocrystalline form for use according to any one of embodiments 151 to 153 wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

Embodiment 161. The cocrystalline form for use according to any one of embodiments 151 to 153, wherein the FGFR3-associated cancer is high risk non-muscle invasive bladder cancer.

Embodiment 162. The cocrystalline form for use according to any one of embodiments 151 to 153, wherein the FGFR3-associated cancer is muscle invasive bladder cancer.

Embodiment 163. Use of the cocrystalline forms according to any one of embodiments 94 to 137 in the manufacture of a medicament for treatment of a FGFR3-associated cancer.

Embodiment 164. The use of embodiment 163, wherein the FGFR3-associated cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

Embodiment 165. The use of embodiments 163 or 164, wherein the FGFR3-associated cancer is selected from the group consisting of urothelial cancer, bladder cancer, urothelial bladder cancer, advanced urothelial bladder cancer, metastatic urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, and muscle invasive bladder cancer.

Embodiment 166. The use of any one of embodiments 163 to 165, wherein the FGFR3-associated cancer is urothelial cancer.

Embodiment 167. The use of any one of embodiments 163 to 165, wherein the FGFR3-associated cancer is bladder cancer.

Embodiment 168. The use of any one of embodiments 163 to 165, wherein the FGFR3-associated cancer is urothelial bladder cancer.

Embodiment 169. The use of any one of embodiments 163 to 165, wherein the FGFR3-associated cancer is advanced urothelial bladder cancer.

Embodiment 170. The use of any one of embodiments 163 to 165, wherein the FGFR3-associated cancer is metastatic urothelial bladder cancer.

Embodiment 171. The use of any one of embodiments 163 to 165, wherein the FGFR3-associated cancer is non-muscle invasive bladder cancer.

Embodiment 172. The use of any one of embodiments 163 to 165, wherein the FGFR3-associated cancer is intermediate risk non-muscle invasive bladder cancer.

Embodiment 173. The use of any one of embodiments 163 to 165, wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

Embodiment 174. The use of any one of embodiments 163 to 165, wherein the FGFR3-associated cancer is high risk non-muscle invasive bladder cancer.

Embodiment 175. The use of any one of embodiments 163 to 165, wherein the FGFR3-associated cancer is non-muscle invasive urothelial cancer.

Embodiment 176. A method for the preparation of the cocrystalline form according to any one of embodiments 94 to 104, comprising the steps of:

adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2:

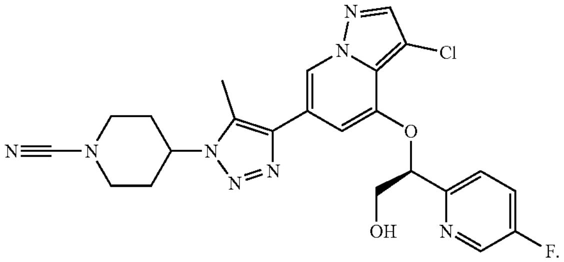 [SMILES: Cc1c(-c2cc(O[C@H](CO)c3ccc(F)cn3)c3c(Cl)cnn3c2)nnn1C1CCN(C#N)CC1]

and gallic acid to a solvent to give a slurry, and adding cyclopentyl methyl ether to the slurry to form a white precipitate.

Embodiment 177. The method of embodiment 176, wherein the solvent is THF.

Embodiment 178. The method of embodiments 176 or 177, wherein the slurry is seeded with the cocrystalline form:

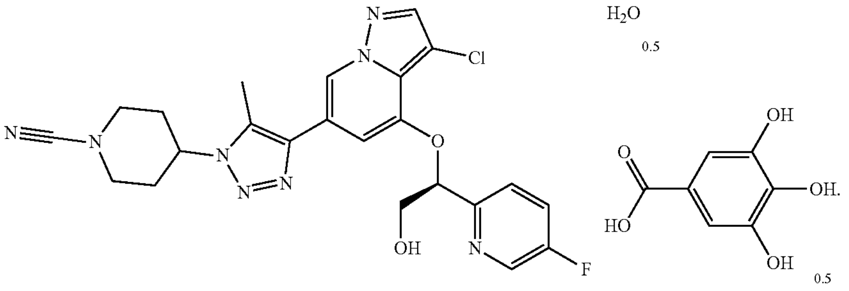

Embodiment 179. A method for the preparation of the cocrystalline form according to any one of embodiments 94 to 96, 98 to 104, comprising the step of heating

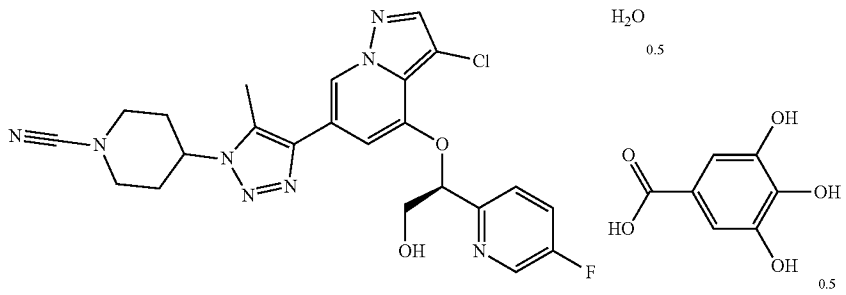

to form a dehydrated hydrate.

Embodiment 180. A method for the preparation of the cocrystalline form according to any one of embodiments 94, 114 to 120, comprising the step of combining

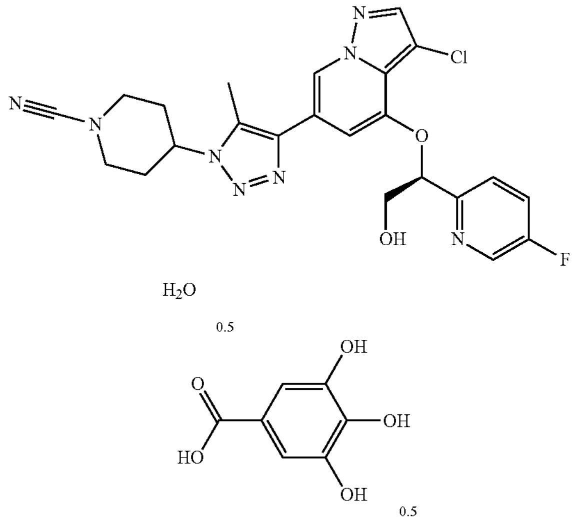

with acetonitrile.

Embodiment 181. A method for the preparation of the cocrystalline form according to any one of embodiments 121 to 128, comprising the step of adding gallic acid to

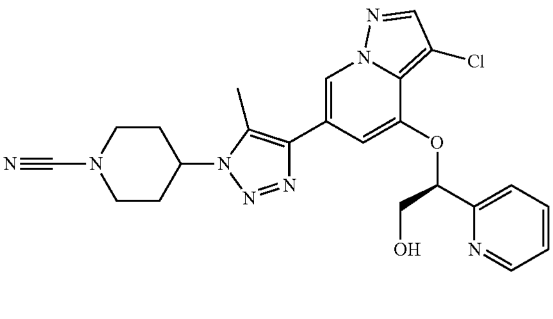 [SMILES: Cc1c(-c2cc(O[C@H](CO)c3ccccn3)c3c(Cl)cnn3c2)nnn1C1CCN(C#N)CC1]

dissolved in ethyl acetate.

Embodiment 182. A method for the preparation of the cocrystalline form according to any one of embodiments 121, 130 to 136, comprising the step of dissolving

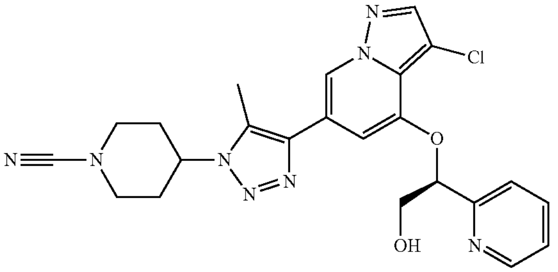 [SMILES: Cc1c(-c2cc(O[C@H](CO)c3ccccn3)c3c(Cl)cnn3c2)nnn1C1CCN(C#N)CC1]

in ethyl acetate saturated with nicotinamide.

What is claimed is:

1. A cocrystalline form of ("Isomer2")

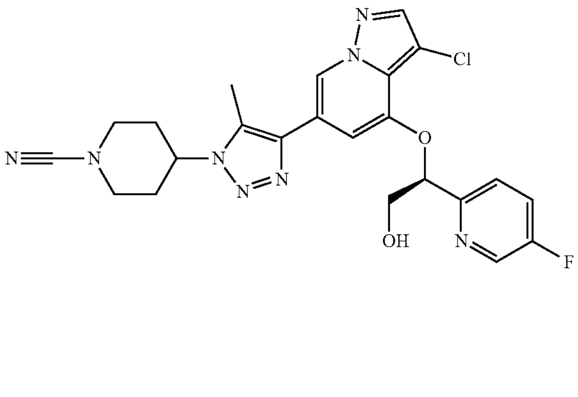 [SMILES: Cc1c(-c2cc(O[C@H](CO)c3ccc(F)cn3)c3c(Cl)cnn3c2)nnn1C1CCN(C#N)CC1]

and a gallic acid coformer.

2. The cocrystalline form of claim 1 wherein the ratio of Isomer 2 to gallic acid is about 2:1.

3. The cocrystalline form of claim 1 wherein water content ranges from about 0% to about 3.2%.

4. The cocrystalline form of claim 1 wherein the cocrystalline form is

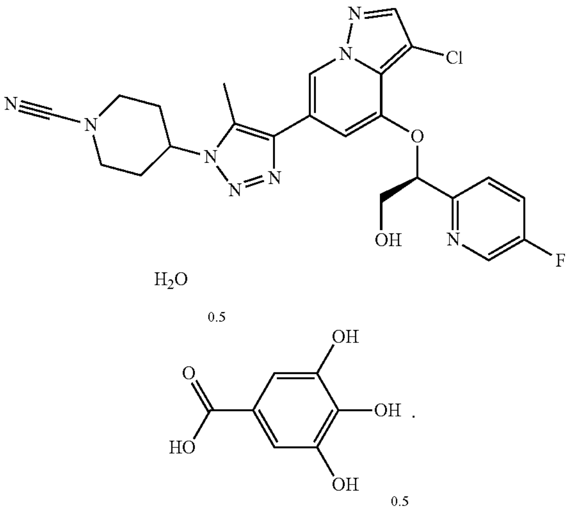

5. The cocrystalline form of claim 4 that is dehydrated or partially dehydrated.

6. The cocrystalline form of claim 1 wherein the cocrystalline form is

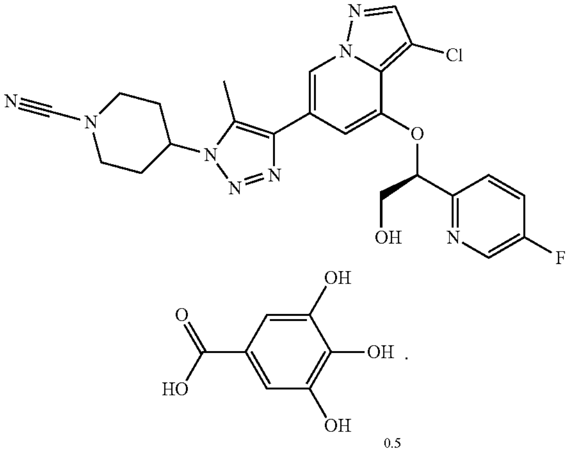

7. The cocrystalline form of claim 1 characterized by having an XRPD pattern using CuKα radiation comprising a peak at 8.4° and one or more peaks at 6.7°, 9.2°, 10.0°, 13.4°, 14.1°, 15.6°, 16.9°, 18.4°, 19.6°, 21.3°, 23.4°, or 24.2° with a tolerance for the diffraction angles of ±0.2 degrees.

8. The cocrystalline form of claim 1 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4°; with a tolerance for the diffraction angles of ±0.2 degrees.

9. The cocrystalline form of claim 8 characterized by an XRPD pattern using CuKα radiation having a diffraction peak at diffraction angle 2-theta of 8.4° in combination with two or more of the peaks selected from the group consisting of 15.6°, 21.3°, 6.7°, and 23.4°; with a tolerance for the diffraction angles of ±0.2 degrees.

10. The cocrystalline form of claim 9 characterized by an XRPD pattern using CuKα radiation having a diffraction peak at diffraction angle 2-theta of 8.4° in combination with three or more of the peaks selected from the group consisting of 15.6°, 21.3°, 6.7°, and 23.4°; with a tolerance for the diffraction angles of ±0.2 degrees.

11. The cocrystalline form of claim 8 characterized by an XRPD pattern using CuKα radiation having a diffraction peak at diffraction angle 2-theta of 8.4° in combination with one or more of the peaks selected from the group consisting of 15.6°, 21.3°, 6.7°, and 23.4° and in combination with one or more of the peaks selected from the group consisting of 9.2°, 10.0°, 13.4°, 14.10, 16.9°, 18.4°, 19.6°, and 24.2° with a tolerance for the diffraction angles of ±0.2 degrees.

12. The cocrystalline form of claim 1 characterized by a $^{13}C$ solid state NMR spectrum which comprises peaks referenced to the carbonyl resonance of glycine selected from the group consisting of 8.1, 11.1, 26.6, 28.2, 32.3, 35.0, 80.7, 81.7, 99.6, 102.3, 110.9, 158.0, 160.0, 168.2, and 175.0, with a tolerance of ±0.2 ppm.

13. A cocrystalline form,

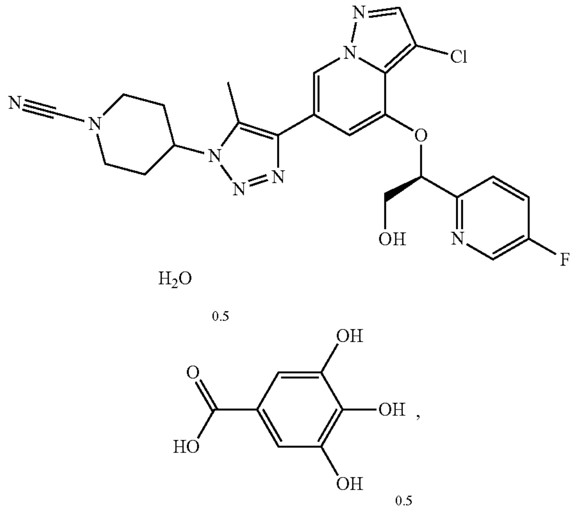

obtainable by adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2 and gallic acid to a solvent to give a slurry, and adding cyclopentyl methyl ether to the slurry to form a white precipitate, wherein the crystalline form has improved solubility relative to a freebase form of Isomer 2:

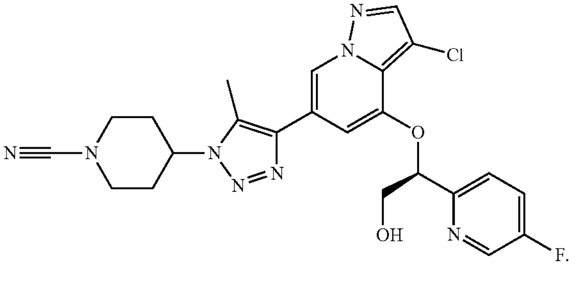 [SMILES: Cc1c(-c2cc(O[C@H](CO)c3ccc(F)cn3)c3c(Cl)cnn3c2)nnn1C1CCN(C#N)CC1]

14. The cocrystalline form of claim 13, wherein the solvent comprises THF.

15. The cocrystalline form of claim 13 wherein the slurry is seeded with the cocrystalline form.

16. A cocrystalline form,

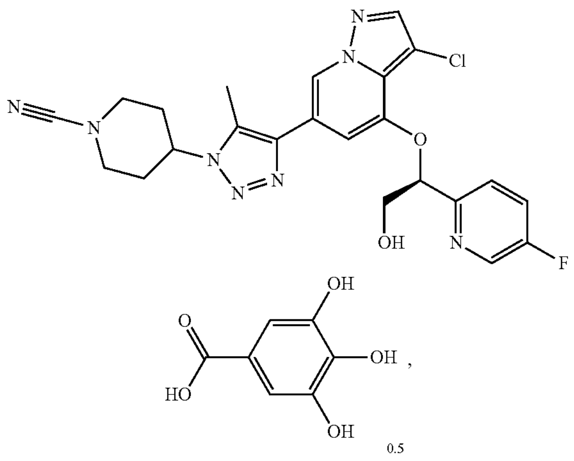

obtainable by heating

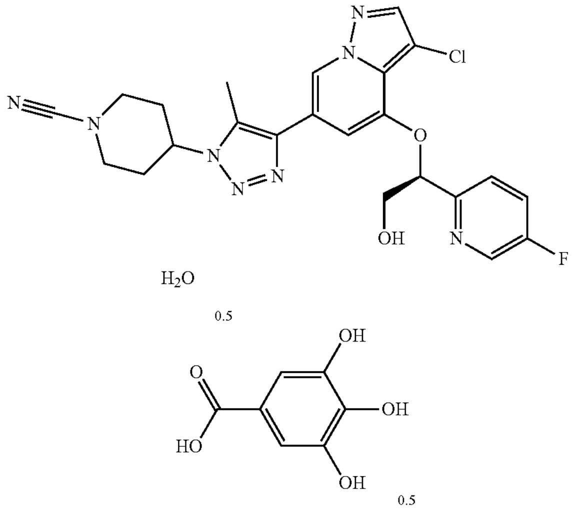

to form a dehydrated hydrate wherein the crystalline form has improved solubility relative to a freebase form of Isomer 2:

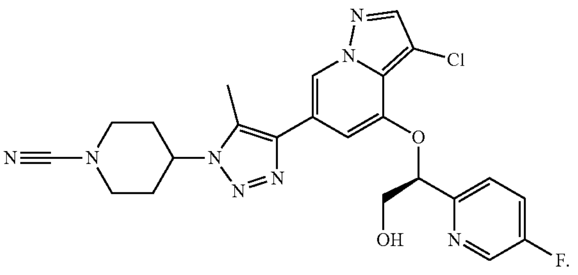 [SMILES: Cc1c(-c2cc(O[C@H](CO)c3ccc(F)cn3)c3c(Cl)cnn3c2)nnn1C1CCN(C#N)CC1]

17. The cocrystalline form of claim 16 wherein the step of heating is from approximately 25° C. to 200° C. at a rate of 10° C./min.

18. The cocrystalline form of claim 16 wherein nitrogen is a carrier gas at about 10 mL/min.

19. The cocrystalline form of claim 16 wherein nitrogen is a purge gas at about 50 mL/min.

20. The cocrystalline form of claim 1 wherein the ratio of Isomer 2 to gallic acid is about 1:1.

21. The cocrystalline form of claim 20 wherein the cocrystalline form is

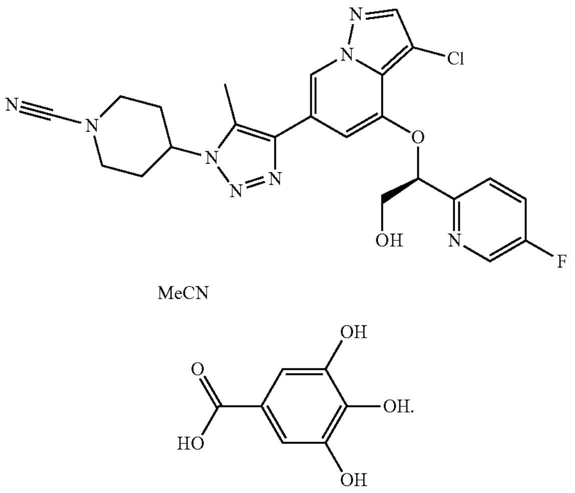

22. The cocrystalline form of claim 20 characterized by having an XRPD pattern using CuKα radiation comprising a peak at 14.6° and one or more peaks at 5.7°, 6.5°, 9.8°, 13.0°, 13.5°, 16.5°, 17.10, 18.9°, 19.7°, 23.8°, or 24.5° with a tolerance for the diffraction angles of ±0.2 degrees.

23. The cocrystalline form of claim 22 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7°; with a tolerance for the diffraction angles of ±0.2 degrees.

24. The cocrystalline form of claim 23 characterized by an XRPD pattern using CuKα radiation having a diffraction peak at diffraction angle 2-theta of 14.6° in combination with two or more of the peaks selected from the group consisting of 9.8°, 23.8°, 6.5°, and 19.7°; with a tolerance for the diffraction angles of ±0.2 degrees.

25. The cocrystalline form of claim 24 characterized by an XRPD pattern using CuKα radiation having a diffraction peak at diffraction angle 2-theta of 14.6° in combination with three or more of the peaks selected from the group consisting of 9.8°, 23.8°, 6.5°, and 19.7°; with a tolerance for the diffraction angles of ±0.2 degrees.

26. The cocrystalline form of claim 22 characterized by an XRPD pattern using CuKα radiation having a diffraction peak at diffraction angle 2-theta of 14.6° in combination with one or more of the peaks selected from the group consisting of 9.8°, 23.8°, 6.5°, and 19.7° and in combination with one or more of the peaks selected from the group consisting of 5.7°, 13.0°, 13.5°, 16.5°, 17.10, 18.9°, and 24.5° with a tolerance for the diffraction angles of ±0.2 degrees.

27. A cocrystalline form,

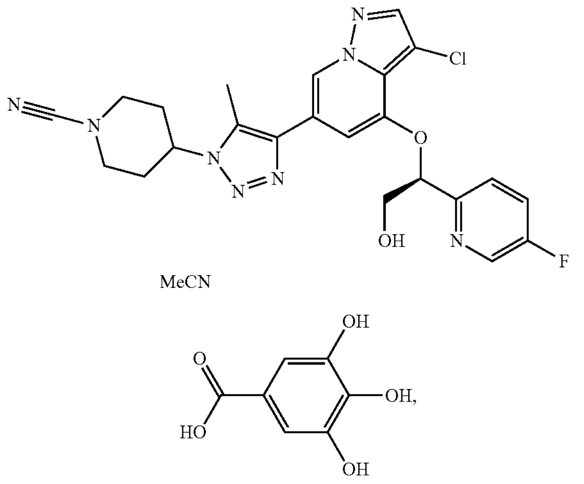

obtainable by combining

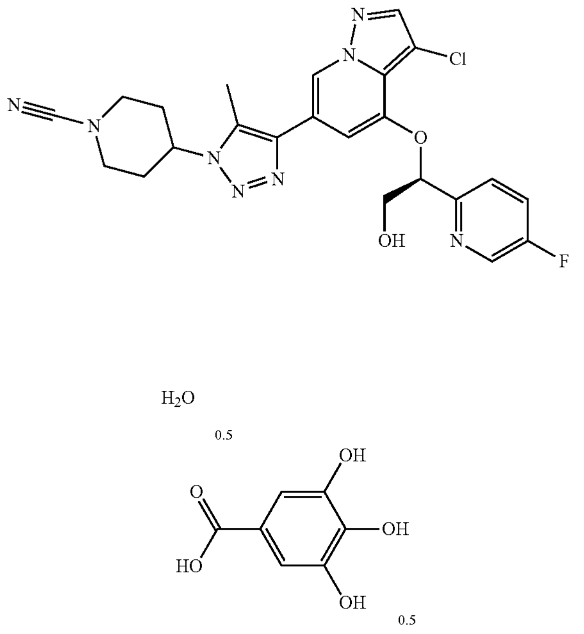

with acetonitrile, wherein the crystalline form has improved solubility relative to a freebase form of Isomer 2:

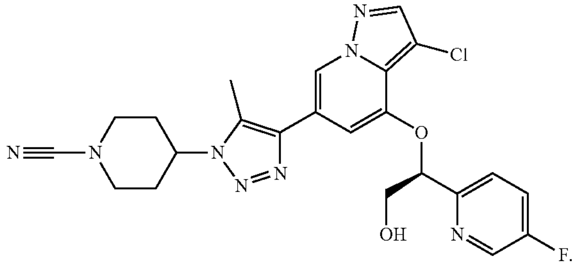

28. A cocrystalline form of Isomer A:

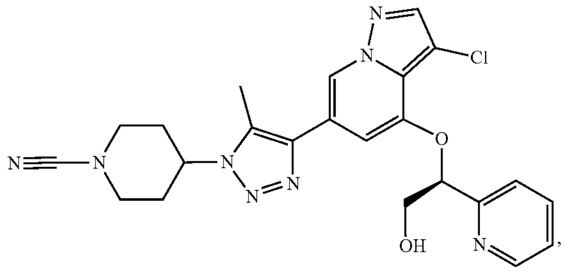 [SMILES: Cc1c(-c2cc(O[C@H](CO)c3ccccn3)c3c(Cl)cnn3c2)nnn1C1CCN(C#N)CC1]

and a gallic acid coformer or a nicotinamide coformer.

29. The cocrystalline form of claim 28 wherein the ratio of Isomer A to gallic acid is about 1:1.

30. The cocrystalline form of claim 28 wherein the cocrystalline form is

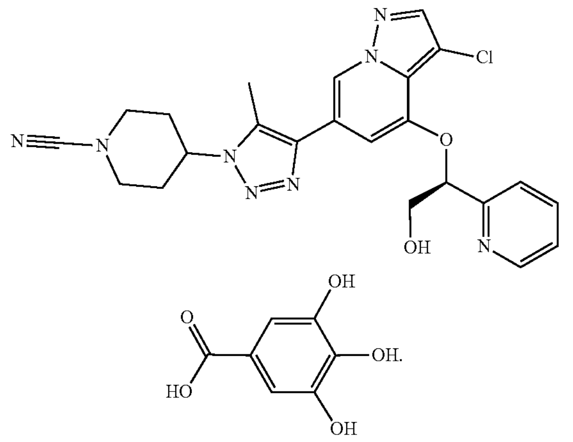

31. The cocrystalline form of claim 28 characterized by having an XRPD pattern using CuKα radiation comprising a peak at 6.9° and one or more peaks at 9.10, 10.5°, 12.7°, 15.7°, 16.3°, 16.8°, 17.10, 17.9°, 18.4°, 21.0°, or 23.4° with a tolerance for the diffraction angles of ±0.2 degrees.

32. The cocrystalline form of claim 31 characterized by having an XRPD pattern using CuKα radiation comprising a peak at 6.9° in combination with one or more of the peaks selected from the group consisting of 12.7°, 18.4°, 9.10, and 23.4° with a tolerance for the diffraction angles of ±0.2 degrees.

33. The cocrystalline form of claim 32 characterized by having an XRPD pattern using CuKα radiation comprising a peak at 6.9° in combination with two or more of the peaks selected from the group consisting of 12.7°, 18.4°, 9.10, and 23.4° with a tolerance for the diffraction angles of ±0.2 degrees.

34. The cocrystalline form of claim 33 characterized by having an XRPD pattern using CuKα radiation comprising a peak at 6.9° in combination with three or more of the peaks selected from the group consisting of 12.7°, 18.4°, 9.10, and 23.4° with a tolerance for the diffraction angles of ±0.2 degrees.

35. The cocrystalline form of claim 31 characterized by having an XRPD pattern using CuKα radiation comprising a peak at 6.9° in combination with one or more of the peaks selected from the group consisting of 12.7°, 18.4°, 9.10, and 23.4° and in combination with one or more of the peaks selected from the group consisting of 9.10, 10.5°, 12.7°, 15.7°, 16.3°, 16.8°, 17.10, 17.9°, 18.4°, 21.0°, and 23.4° with a tolerance for the diffraction angles of ±0.2 degrees.

36. A cocrystalline form,

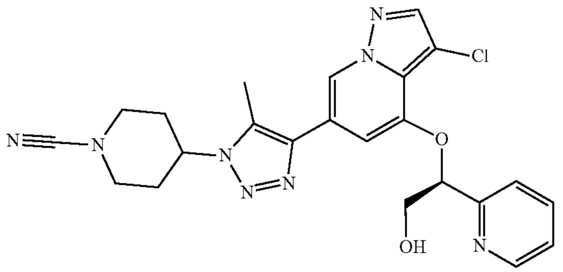

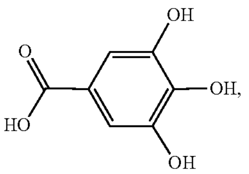

obtainable by adding gallic acid to

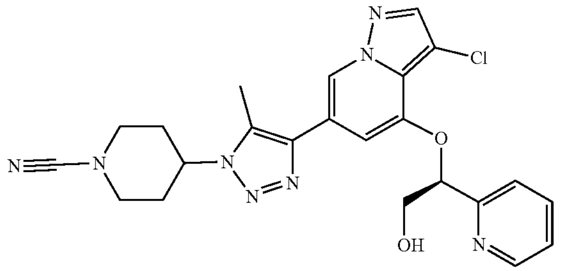 [SMILES: Cc1c(-c2cc(O[C@H](CO)c3ccccn3)c3c(Cl)cnn3c2)nnn1C1CCN(C#N)CC1]

dissolved in ethyl acetate, wherein the crystalline form has improved solubility relative to a freebase form of Isomer A:

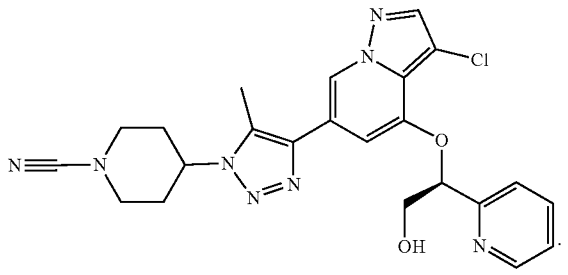 [SMILES: Cc1c(-c2cc(O[C@H](CO)c3ccccn3)c3c(Cl)cnn3c2)nnn1C1CCN(C#N)CC1]

37. The cocrystalline form of claim 28 wherein the ratio of Isomer A to nicotinamide is about 1:1.

38. The cocrystalline form of claim 37 wherein the cocrystalline form is

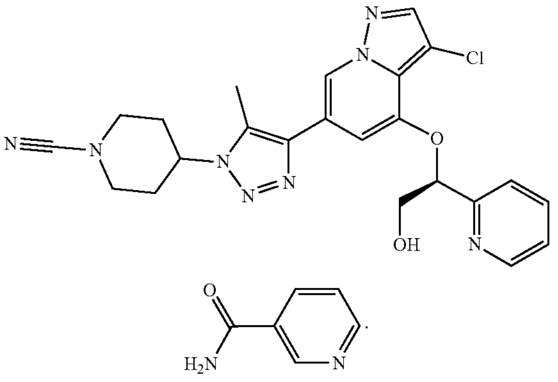

39. The cocrystalline form of claim 28 characterized by having an XRPD pattern using CuKα radiation comprising a peak at 13.7° and one or more peaks at 6.8°, 8.2°, 9.6°, 12.3°, 15.8°, 17.5°, 17.9°, 18.7°, 19.0°, 22.2°, 22.9°, 24.7°, or 26.10 with a tolerance for the diffraction angles of ±0.2 degrees.

40. The cocrystalline form of claim 39 characterized by having an XRPD pattern using CuKα radiation comprising a peak at 13.7° in combination with one or more of the peaks selected from the group consisting of 9.6°, 17.9°, and 24.7° with a tolerance for the diffraction angles of ±0.2 degrees.

41. The cocrystalline form of claim 40 characterized by having an XRPD pattern using CuKα radiation comprising a peak at 13.7° in combination with two or more of the peaks selected from the group consisting of 9.6°, 17.9°, and 24.7° with a tolerance for the diffraction angles of ±0.2 degrees.

42. The cocrystalline form of claim 41 characterized by having an XRPD pattern using CuKα radiation comprising a peak at 13.7° in combination with the peaks selected from the group consisting of 9.6°, 17.9°, and 24.7° with a tolerance for the diffraction angles of ±0.2 degrees.

43. The cocrystalline form of claim 28 characterized by having an XRPD pattern using CuKα radiation comprising a peak at 13.7° in combination with one or more of the peaks selected from the group consisting of 9.6°, 17.9°, and 24.7° and in combination with one or more of the peaks selected from the group consisting of 6.8°, 8.2°, 12.3°, 15.8°, 17.5°, 18.7°, 19.0°, 22.2°, 22.9°, and 26.10 with a tolerance for the diffraction angles of ±0.2 degrees.

44. A cocrystalline form,

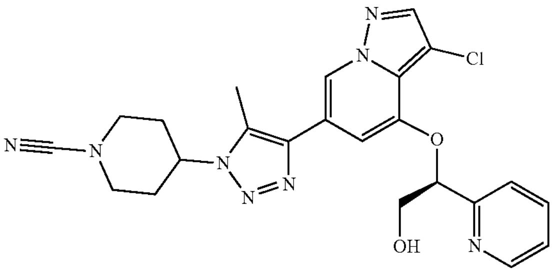

-continued

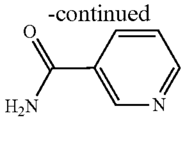

, or a pharmaceutically acceptable salt thereof, obtainable by dissolving

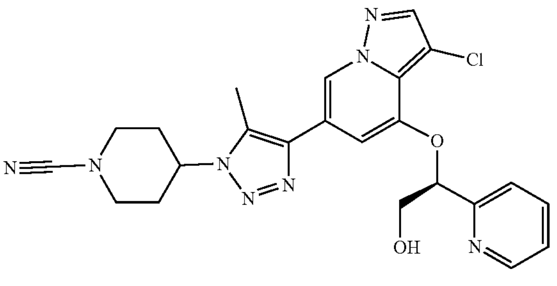 [SMILES: Cc1c(-c2cc(O[C@H](CO)c3ccccn3)c3c(Cl)cnn3c2)nnn1C1CCN(C#N)CC1]

in ethyl acetate saturated with nicotinamide, wherein the crystalline form has improved solubility relative to a freebase form of Isomer A:

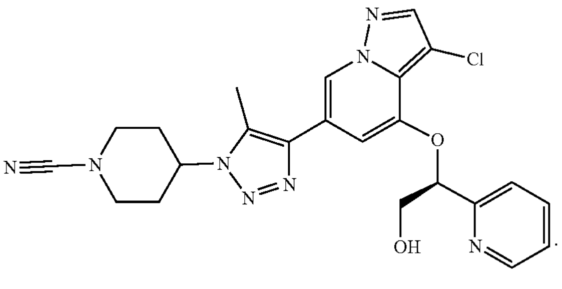 [SMILES: Cc1c(-c2cc(O[C@H](CO)c3ccccn3)c3c(Cl)cnn3c2)nnn1C1CCN(C#N)CC1]

.

45. A pharmaceutical composition comprising the cocrystalline form according to claim 1 and further comprising a pharmaceutically acceptable carrier, diluent or excipient.

46. The pharmaceutical composition of claim 45, wherein the composition contains at least about 80% by wt. of the cocrystalline form.

47. The pharmaceutical composition of claim 46, wherein the composition contains at least about 90% by wt. of any of the cocrystalline forms.

48. The pharmaceutical composition of claim 47 wherein the composition contains at least about 95% by wt. of any of the cocrystalline forms.

49. A method of treating a FGFR3-associated cancer comprising administering to a patient in need thereof an effective amount of a cocrystalline form according to claim 1.

50. A method of treating a FGFR3-associated cancer comprising administering to a patient in need thereof an effective amount of the pharmaceutical compositions according to claim 45.

51. The method of claim 49, wherein the FGFR3-associated cancer is selected from the group consisting of breast cancer, invasive ductal breast cancer, invasive lobular breast cancer, lung cancer, non-small-cell lung cancer, lung adenocarcinoma, squamous cell lung cancer, small-cell lung cancer, urothelial cancer, bladder cancer, urothelial bladder cancer, advanced urothelial cancer, advanced urothelial bladder cancer, metastatic urothelial cancer, metastatic urothelial bladder cancer, non-muscle invasive urothelial cancer, non-muscle invasive bladder cancer, muscle invasive urothelial cancer, muscle invasive bladder cancer, upper tract cancer, urothelial upper tract cancer, urethral cancer, gastric cancer, pancreatic cancer, prostate cancer, colorectal cancer, multiple myeloma, liver cancer, melanoma, cutaneous melanoma, head and neck cancer, oral cancer, thyroid cancer, renal cancer, renal pelvis cancer, glioblastoma, endometrial cancer, cervical cancer, ovarian cancer, and testicular cancer.

52. The method of claim 51, wherein FGFR3-associated the cancer is selected from the group consisting of urothelial cancer, bladder cancer, urothelial bladder cancer, advanced urothelial bladder cancer, metastatic urothelial bladder cancer, non-muscle invasive bladder cancer, and muscle invasive bladder cancer.

53. The method of claim 52, wherein the FGFR3-associated cancer is urothelial cancer.

54. The method of claim 52, wherein the FGFR3-associated cancer is intermediate risk non-muscle invasive bladder cancer.

55. The method of claim 52, wherein the FGFR3-associated cancer is Bacillus Calmette-Guerin (BCG)-unresponsive non-muscle invasive bladder cancer or Bacillus Calmette-Guerin (BCG) recurrent non-muscle invasive bladder cancer.

56. The method of claim 52, wherein the FGFR3-associated cancer is high risk non-muscle invasive bladder cancer.

57. A method for the preparation of the cocrystalline form according to claim 4, comprising the steps of:

adding 4-[4-[3-Chloro-4-[1-(5-fluoro-2-pyridyl)-2-hydroxy-ethoxy]pyrazolo[1,5-a]pyridin-6-yl]-5-methyl-triazol-1-yl]piperidine-1-carbonitrile, Isomer 2:

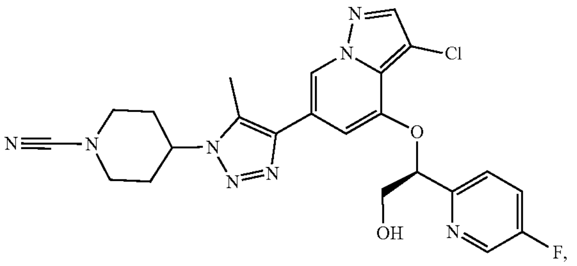 [SMILES: Cc1c(-c2cc(O[C@H](CO)c3ccc(F)cn3)c3c(Cl)cnn3c2)nnn1C1CCN(C#N)CC1]

, and gallic acid to a solvent to give a slurry, and adding cyclopentyl methyl ether to the slurry to form a white precipitate.

58. The method of claim 57, wherein the solvent is THF.

59. The method of claim 57, wherein the slurry is seeded with the cocrystalline form:

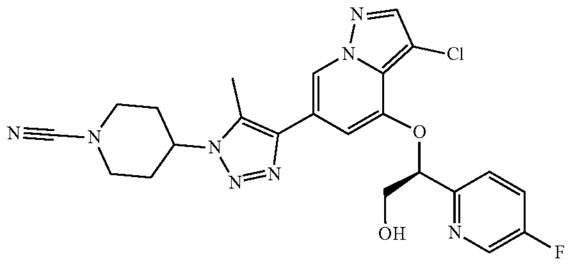

-continued

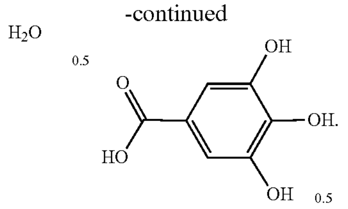

60. A method for the preparation of the cocrystalline form according to claim 6, comprising the step of heating

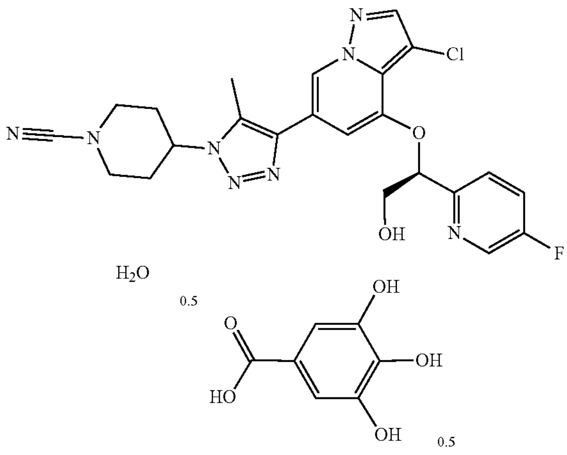

to form a dehydrated hydrate.

61. A method for the preparation of the cocrystalline form according to claim 21, comprising the step of combining

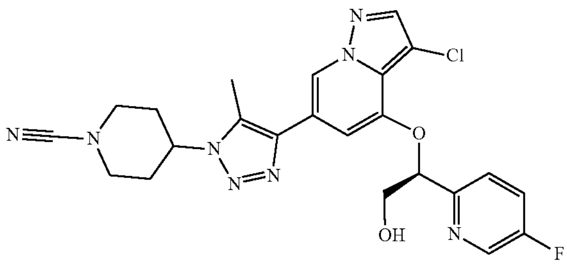

-continued

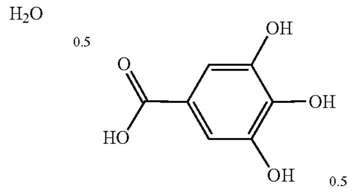

with acetonitrile.

62. A method for the preparation of the cocrystalline form according to claim 30, comprising the step of adding gallic acid to

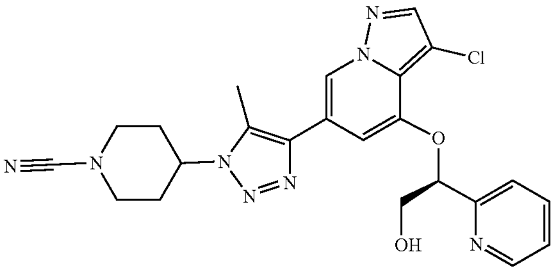 [SMILES: Cc1c(-c2cc(O[C@H](CO)c3ccccn3)c3c(Cl)cnn3c2)nnn1C1CCN(C#N)CC1]

dissolved in ethyl acetate.

63. A method for the preparation of the cocrystalline form according to claim 38, comprising the step of dissolving

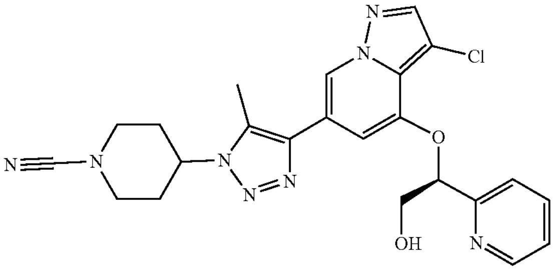 [SMILES: Cc1c(-c2cc(O[C@H](CO)c3ccccn3)c3c(Cl)cnn3c2)nnn1C1CCN(C#N)CC1]

in ethyl acetate saturated with nicotinamide.

* * * * *